(12) United States Patent
Arora et al.

(10) Patent No.: US 9,440,043 B2
(45) Date of Patent: Sep. 13, 2016

(54) CATHETER HAVING A TAPERED STRUCTURE AND BALLOON FORMED ABOVE A LOWER DRAINAGE HOLE

(71) Applicant: Leading Age Supplies LLC, Cleveland, OH (US)

(72) Inventors: Billy K. Arora, Shaker Heights, OH (US); Pradip P. Kamat, Orange Village, OH (US)

(73) Assignee: LEADING AGE SUPPLIES LLC, Cleveland, OH (US)

( * ) Notice: Subject to any disclaimer, the term of this patent is extended or adjusted under 35 U.S.C. 154(b) by 0 days.

(21) Appl. No.: 14/633,823

(22) Filed: Feb. 27, 2015

(65) Prior Publication Data

US 2015/0359996 A1 Dec. 17, 2015

Related U.S. Application Data

(60) Provisional application No. 62/012,249, filed on Jun. 13, 2014.

(51) Int. Cl.
*A61M 25/10* (2013.01)
*A61M 25/00* (2006.01)
(Continued)

(52) U.S. Cl.
CPC ...... *A61M 25/0017* (2013.01); *A61B 5/14507* (2013.01); *A61B 5/20* (2013.01); *A61B 5/207* (2013.01); *A61B 5/6852* (2013.01); *A61M 25/0023* (2013.01); *A61M 25/0045* (2013.01); *A61M 25/0068* (2013.01); *A61B 1/00082* (2013.01); *A61B 1/307* (2013.01); *A61B 5/0002* (2013.01); *A61B 5/01* (2013.01); *A61B 5/14539* (2013.01); *A61B 5/6853* (2013.01); *A61B 2562/0219* (2013.01);
(Continued)

(58) Field of Classification Search
CPC .......... A61M 25/10; A61M 25/0017; A61M 2025/1043; A61M 2025/1059; A61M 2025/107; A61M 2025/1072; A61M 2025/1086; A61M 2025/1093; A61M 25/0021; A61M 2210/1078; A61M 2210/1085; A61M 2210/1089; A61M 2210/1092; A61M 2210/1096; A61M 25/001
See application file for complete search history.

(56) References Cited

U.S. PATENT DOCUMENTS 3,811,448 A * 5/1974 Morton .................. 604/102.02
3,867,945 A * 2/1975 Long .................... A61M 25/00
604/170.02

(Continued)

FOREIGN PATENT DOCUMENTS

| KR | WO 2014196763 A1 * | 12/2014 | ........ A61M 25/0043 |
|---|---|---|---|
| WO | 0211810 | 2/2002 | |
| WO | 2013074763 | 5/2013 | |

OTHER PUBLICATIONS

International Search Report and Written Opinion for International Patent Application Serial No. PCT/US15/19140, dated Jul. 27, 2015, 19 pages.

*Primary Examiner* — Adam Marcetich
(74) *Attorney, Agent, or Firm* — Amin, Turocy & Watson, LLP

(57) ABSTRACT

A indwelling or Foley catheter is provided that has a tapered structure. In an aspect, the catheter includes an elongated cylindrical body having a proximal end configured to lie inside the bladder when inserted into the urinary tract and a distal end configured to extend outside the urinary tract, wherein an outer diameter of the proximal end is larger than an outer diameter of the distal end.

30 Claims, 22 Drawing Sheets

(51) Int. Cl.
*A61B 5/20* (2006.01)
*A61B 5/145* (2006.01)
*A61B 5/01* (2006.01)
*A61B 5/00* (2006.01)
*A61M 25/01* (2006.01)
*A61B 1/00* (2006.01)
*A61B 1/307* (2006.01)

(52) U.S. Cl.
CPC ........... *A61B 2562/0247* (2013.01); *A61B 2562/0271* (2013.01); *A61M 25/0102* (2013.01); *A61M 25/10* (2013.01); *A61M 25/1002* (2013.01); *A61M 2205/3303* (2013.01); *A61M 2205/3584* (2013.01); *A61M 2205/3592* (2013.01); *A61M 2205/50* (2013.01); *A61M 2210/1085* (2013.01); *A61M 2210/1089* (2013.01)

(56) References Cited

U.S. PATENT DOCUMENTS

| | | | |
|---|---|---|---|
| 3,889,686 A | 6/1975 | Duturbure | |
| 4,222,384 A * | 9/1980 | Birtwell | 604/103 |
| 4,655,750 A * | 4/1987 | Vaillancourt | 604/165.01 |
| 4,909,785 A * | 3/1990 | Burton et al. | 604/544 |
| 5,250,029 A * | 10/1993 | Lin et al. | 604/103.11 |
| 5,454,798 A | 10/1995 | Kubalak et al. | |
| 5,628,755 A * | 5/1997 | Heller | A61F 2/958 |
| | | | 604/96.01 |
| 5,656,013 A | 8/1997 | Yoon | |
| 5,707,357 A | 1/1998 | Mikhail et al. | |
| 5,931,831 A * | 8/1999 | Linder | A61M 25/0026 |
| | | | 604/264 |
| 6,203,532 B1 * | 3/2001 | Wright | 604/264 |
| 2002/0091355 A1 * | 7/2002 | Hayden | A61M 25/0074 |
| | | | 604/104 |
| 2002/0173816 A1 * | 11/2002 | Hung | A61M 25/0068 |
| | | | 606/194 |
| 2003/0176886 A1 * | 9/2003 | Wholey | A61F 2/013 |
| | | | 606/200 |
| 2005/0288639 A1 | 12/2005 | Hibner | |
| 2006/0004316 A1 * | 1/2006 | Difiore et al. | 604/6.16 |
| 2006/0116661 A1 * | 6/2006 | Tanghoej | 604/540 |
| 2007/0043390 A1 * | 2/2007 | Neilan | A61F 2/01 |
| | | | 606/200 |
| 2008/0071250 A1 | 3/2008 | Crisp | |
| 2008/0147170 A1 * | 6/2008 | Vrba | A61M 25/00 |
| | | | 623/1.22 |
| 2010/0145286 A1 | 6/2010 | Zhang et al. | |
| 2011/0094655 A1 * | 4/2011 | Wiita et al. | 156/157 |
| 2011/0190737 A1 * | 8/2011 | Rocco | 604/544 |
| 2011/0218520 A1 * | 9/2011 | Andrich | 604/544 |
| 2012/0041419 A1 * | 2/2012 | Blanchard et al. | 604/523 |
| 2012/0108889 A1 * | 5/2012 | Behan | 600/30 |
| 2012/0232496 A1 * | 9/2012 | Lareau | A61M 25/0026 |
| | | | 604/250 |

\* cited by examiner

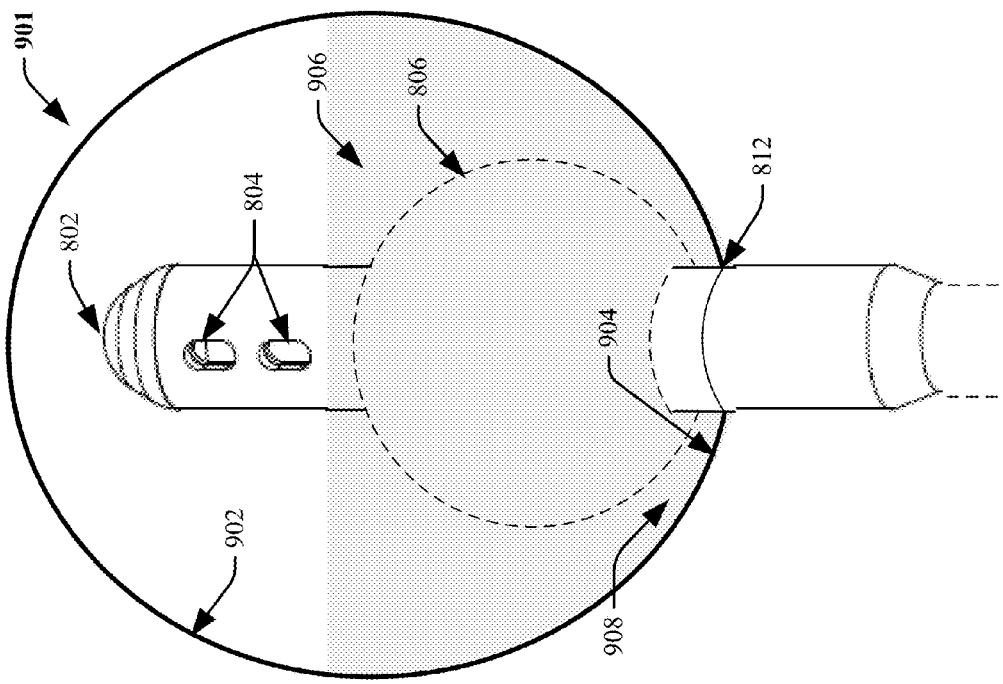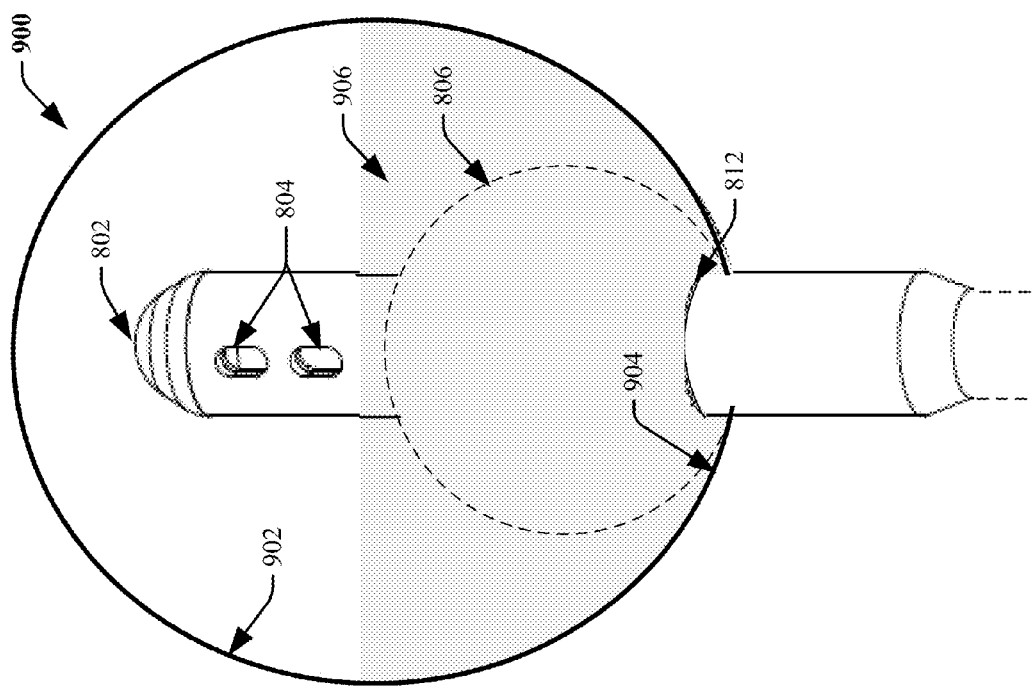
FIG. 9

SECTION A-A

SECTION B-B

SECTION A-A  FIG. 15

SECTION B-B

CATHETER HAVING A TAPERED STRUCTURE AND BALLOON FORMED ABOVE A LOWER DRAINAGE HOLE

RELATED APPLICATION

This application claims priority to U.S. Provisional Patent Application No. 62/012,249 filed on Jun. 13, 2014, and entitled "TAPERED INDWELLING CATHETER." The entirety of the aforementioned application is incorporated by reference herein.

TECHNICAL FIELD

This disclosure relates to catheters having a tapered structure and/or a balloon formed above a lower drainage hole.

BACKGROUND

An indwelling catheter is a catheter that is inserted into the bladder and allowed to remain in the bladder for a few hours to several weeks. A Foley catheter is a common type of indwelling urinary catheter. A Foley catheter generally includes a thin, flexible tube that can be inserted into the bladder to drain urine. It is held in place with a balloon at the end that lies inside the bladder (e.g., referred to herein as the inner or proximal end) which is filled with sterile water or gas to prevent the catheter from being removed from the bladder. The urine drains through the catheter tube into a bag and thereafter expelled. The tube of a Foley catheter has two separated channels, or lumens, running down its length. One lumen is open at both ends and allows urine to drain into a collection bag. The other lumen has a valve on an outside end and connects to the balloon at a tip to allow for inflation of the balloon with sterile water or gas.

A common issue with Foley catheters is introduction of infection into the bladder. Risk of infection in the bladder increases significantly the longer the catheter remains in place. In fact, a recent study has found that more than 30 million Foley catheters are inserted annually in the United States and result in over 1 million nosocomial catheter acquired urinary tract infections (CAUTI's) per year. CAUTI's are the second most common cause of nosocomial bloodstream infections and approximately 3% of all patients with a catheter will develop bacteremia. Approximately 80% of urinary tract infections (UTI's) are associated with indwelling Foley catheters. For an acute care hospitalization, CAUTI's can add $500 to $1,000 in direct costs with an additional $3,800 if bacteremia occurs.

Foley catheter based UTI's are attributable to bacteria growth on the surface of the inserted Foley catheter that advances along the shaft of the catheter into the bladder and eventually into the blood stream. Under this model, bacterial growth is directly associated with presence of the catheter and as bacteria moves up the shaft of the catheter, the patient is likely to develop urethritis (infection of the urethra) and cystitis (infection of the bladder). In addition, Foley catheters can cause unnecessary pressure on urethral mucosa which often results in trauma and ischemic necrosis. For example, a Foley catheter can induce inflammation in the urethra coupled with mucosal injury due to presence of a foreign body. The resultant injury to the mucosa coupled with the presence of the foreign body and absence of normal clearance of dead mucosal cells provides a milieu for bacterial overgrowth. The inflammation can also travel up the prostate and result in prostatitis or into the bladder and cause cystitis.

The degree of mucosal injury associated with an inserted Foley catheter is often directly proportional to the size of the catheter. Generally, the larger the diameter of the Foley catheter tube, the greater the pressure on the urethral mucosa and thus the greater amount of resulting trauma and ischemic necrosis. Accordingly, Foley catheter design has aimed to reduce the diameter of the catheter to a minimal diameter that still provides free flow of urine. However, prior efforts at using extremely small diameter catheters have failed for several reasons. For example, a Foley catheter with a smaller outer lumen naturally requires a smaller inner lumen. However, catheters with small inner lumen tends to become obstructed frequently. In addition, Foley catheters with smaller inner and outer lumens do not have axial and longitudinal rigidity. As a result, insertion becomes very difficult, especially in older patients who might have significant bladder outlet obstruction or prostatic enlargement. Further, a Foley catheter tube with a small diameter can result in urinary leakage around the catheter when inserted. This is especially pertinent to older women with weakness of the bladder sphincter but can also be seen in both genders and all ages.

The above-described deficiencies of conventional indwelling catheters are merely intended to provide an overview of some of problems of current technology, and are not intended to be exhaustive. Other problems with the state of the art, and corresponding benefits of some of the various non-limiting embodiments described herein, may become further apparent upon review of the following detailed description.

BRIEF DESCRIPTION OF THE DRAWINGS

FIG. 9 depicts urine collection within the bladder when having a catheter with only upper drainage holes in accordance with various aspects and embodiments described herein;

DETAILED DESCRIPTION

Figure 1:
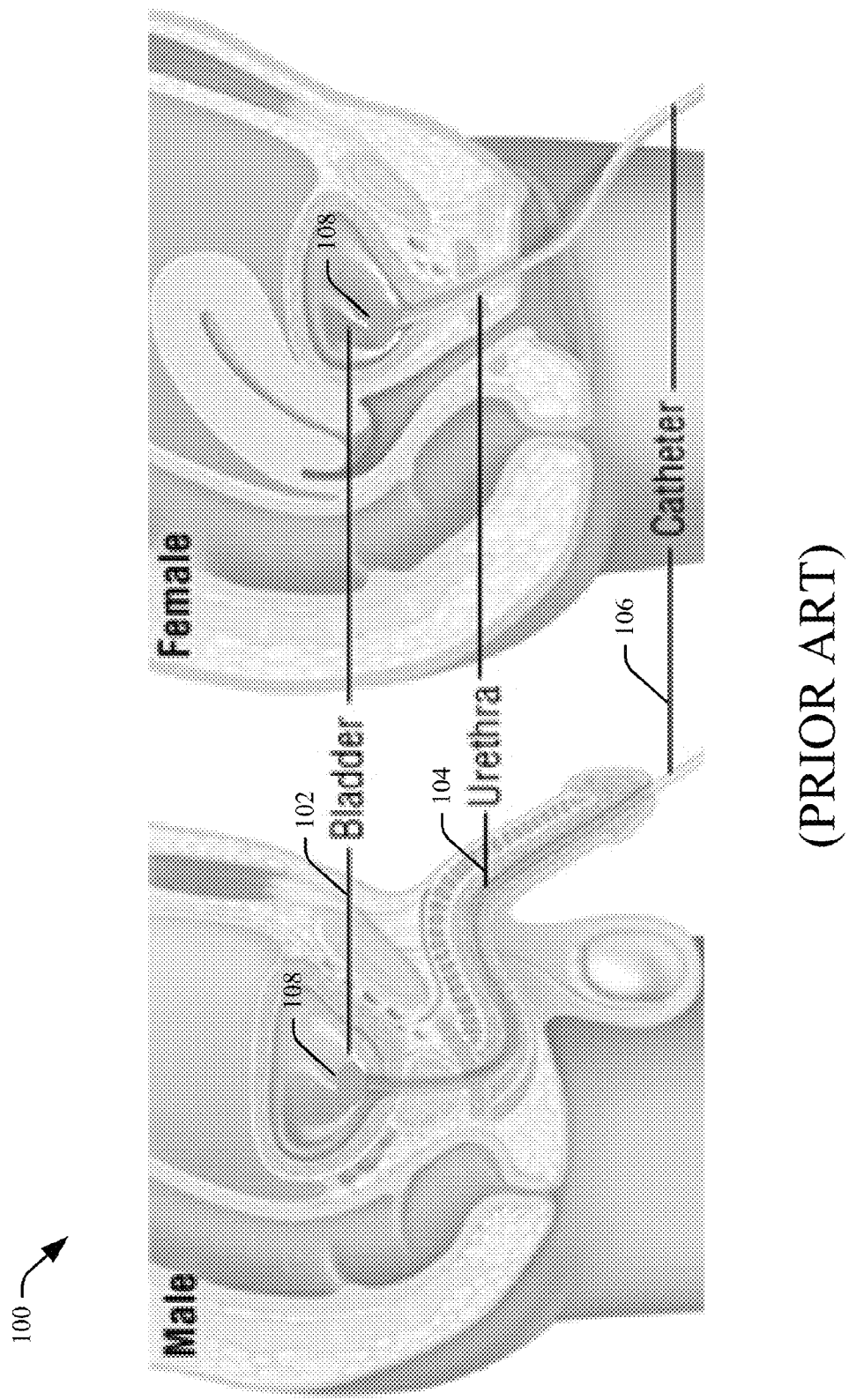
FIG. 1 presents a diagram showing a conventional Foley catheter inserted into the male and female urinary tract in accordance with various aspects and embodiments described herein.

Various aspects or features of this disclosure are described with reference to the drawings, wherein like reference numerals are used to refer to like elements throughout. In this specification, numerous specific details are set forth in order to provide a thorough understanding of the subject disclosure. It should be understood, however, that the certain aspects of this disclosure may be practiced without these specific details, or with other methods, components, materials, etc. In other instances, well-known structures and devices are shown in block diagram form to facilitate describing the subject disclosure.

By way of introduction, the subject matter described in this disclosure relates to a urinary catheter having improved characteristics over existing urinary catheters. In an embodiment, a catheter is disclosed that has a tapered body divided into three sections, an inner portion, a transition portion and a shaft. The inner portion is the portion of the catheter that is located inside of the bladder when the catheter is inserted into the urinary tract. The inner portion of the catheter includes a balloon attached thereto and has a first relatively large diameter. The balloon is connected to the outer lumen of the catheter and serves to anchor the catheter within the bladder when filled with water or air via the outer lumen. The transition portion is the portion of the catheter that lies just outside of and adjacent to the outer wall of the bladder when the catheter is inserted into the urinary track. The transition portion has at least a second medium diameter that is smaller than the first large diameter. In an aspect, the diameter of the transition portion slowly tapers over a fixed distance (e.g., in a funnel like shape). The shaft is the portion of the catheter that connects the transition portion with the outer catheter components that are positioned outside of the body when the catheter is inserted into the urinary tract (e.g., the valve or valves, the collection bag, etc.). When inserted into the urinary tract, the shaft is the portion of the catheter that lies within the urethra and extends outside of the body. The shaft has a third small diameter that is smaller than the second diameter. In an aspect, the subject tapered catheter further includes and/or is employed with an introducer configured to facilitate urinary catheterization. The introducer is later removed following successful catheterization.

By employing a tapered structure, the portion of the catheter located predominantly within the urethra (i.e., the shaft) can have a relatively small diameter (e.g., less than or equal to 5.0 mm), thus reducing the amount of mucosal injury associated with insertion and persistence in the urinary tract. As a result, the growth and promotion of bacteria and infection associated with mucosal injury is reduced. In addition, drainage obstruction associated with catheters having a small diameter and thus a small inner lumen is alleviated due to provision of a larger diameter inner lumen portion within the bladder and the funneling effect provided by the tapered structure. Further, the diameter of the transition portion can be adapted to provide sufficient buttress between the bladder and the urethra to prevent urinary leakage associated with catheters having small diameters while still allowing for a shaft portion with a small diameter. Accordingly, the subject tapered catheter can serve as excellent indwelling or Foley (long term) catheter. However it should be appreciated that the tapered features of the subject catheter can be extended to other types of catheters (e.g., intermittent catheters) or catheters inserted into other body cavities or orifices.

In another embodiment, a urinary catheter is provided that prevents and/or alleviates complications associated with an underactive bladder condition. In an aspect, this urinary catheter includes the following standard catheter features, including a proximal end designed for positioning within the bladder, a distal end designed for positioning outside the urinary tract, an inner portion that extends from the proximal end and is designed to rest inside the bladder, and a balloon attached to the inner portion of the catheter below the proximal end that is designed to rest on the lower inner wall of the bladder. Conventional urinary catheters further include a single drainage opening at the proximal end that allows urine to flow from the bladder into the inner lumen and through the shaft of the catheter to an external drainage opening located outside the body at the distal end of the catheter. This single drainage hole is provided above the balloon (e.g., between the balloon and the proximal end on the inner portion of the catheter). With this conventional design, urine can remain within the bladder below the drainage hole while the catheter is in place. Because this urine is not expelled when the catheter remains in place, the patient is not able to completely empty his or her bladder resulting and thus develops an underactive bladder condition. Further this retained urine acts as a ready culture media for bacterial growth and potentially serves as a nidus for CAUTI In view of the above noted deficiency of the conventional urinary catheter, the urinary catheter of the subject embodiment includes at least one lower drainage opening on the inner portion of the catheter (e.g., the portion located within the bladder) below and/or surrounded by the balloon. According to this embodiment, the balloon can have an irregular shape that does not enclose the at least one lower drainage opening when the catheter is located within the urinary tract and the balloon is filled. In one aspect, the balloon can have a C shape that wraps around a portion of the catheter body while establishing a channel along another portion of the catheter body between the ends of the balloon. The lower drainage opening is provided within a lower region of the channel just above the inner lower wall of the bladder. In another aspect, the balloon can have a substantially spherical shape with at least one lip formed in a lower portion of the balloon adjacent to the inner portion of the catheter just above the inner lower wall of the bladder. For example, the lip can resemble a dome or hemispheroidal hollow in the lower portion of the balloon. This lip can allow for urine to flow beneath the balloon along the inner lower wall of the bladder and into the lip reaching a lower opening located on the inner portion of the catheter exposed by the lip.

Referring now to the drawings, FIG. 1 presents a diagram 100 showing a conventional Foley catheter 106 inserted into the male and female urinary tract. The catheter 106 is inserted through the urethra 104. This is the tube that carries urine from the bladder to the outside of the body. Placement of the Foley catheter 106 involves cleaning of the genital area with a sterile solution. A lubricant jelly is often used on the tip of the catheter to help it go in smoothly. The catheter is inserted into the urethra 104 with the balloon deflated and moved slowly and gently into the bladder 102. When the caregiver performing the catheterization begins to see urine flowing from the catheter, it is known that the catheter has reached the bladder 102. The balloon 108 at the end of the catheter is then filled with sterile water or air. The balloon holds the catheter in place so it does not come out of the bladder. The open end of the catheter is attached to a sterile drainage bag.

A Foley catheter can remain in place for varying lengths of time ranging from a few hours to up to several weeks. The risk of infection in the bladder increases with the number of days the catheter is in place. Foley catheters can cause unnecessary pressure on the urethral mucosa during insertion and following insertion as the catheter is allowed to remain in place. A mucosa or mucous membrane is a lining of mostly endodermal origin and covered in epithelium. The urethra 104 is a mucous membrane that facilitates absorption and secretion. For example, mucus secreted by the urethra 104 traps pathogens in the body, facilitating preventing of disease and infection. Pressure on the urethra 104 or urethra mucosa during and following catheter insertion often results in trauma and ischemic necrosis. In particular, the presence of the inserted Foley catheter 106 induces a local inflammatory reaction in the urethra 104 (foreign body reaction). This inflammation is coupled with mucosal injury due to the presence of a foreign body. The resultant injury to the mucosa coupled with the presence of the foreign body and absence of normal clearance of dead mucosal cells provides a milieu for bacterial overgrowth.

Figure 2:
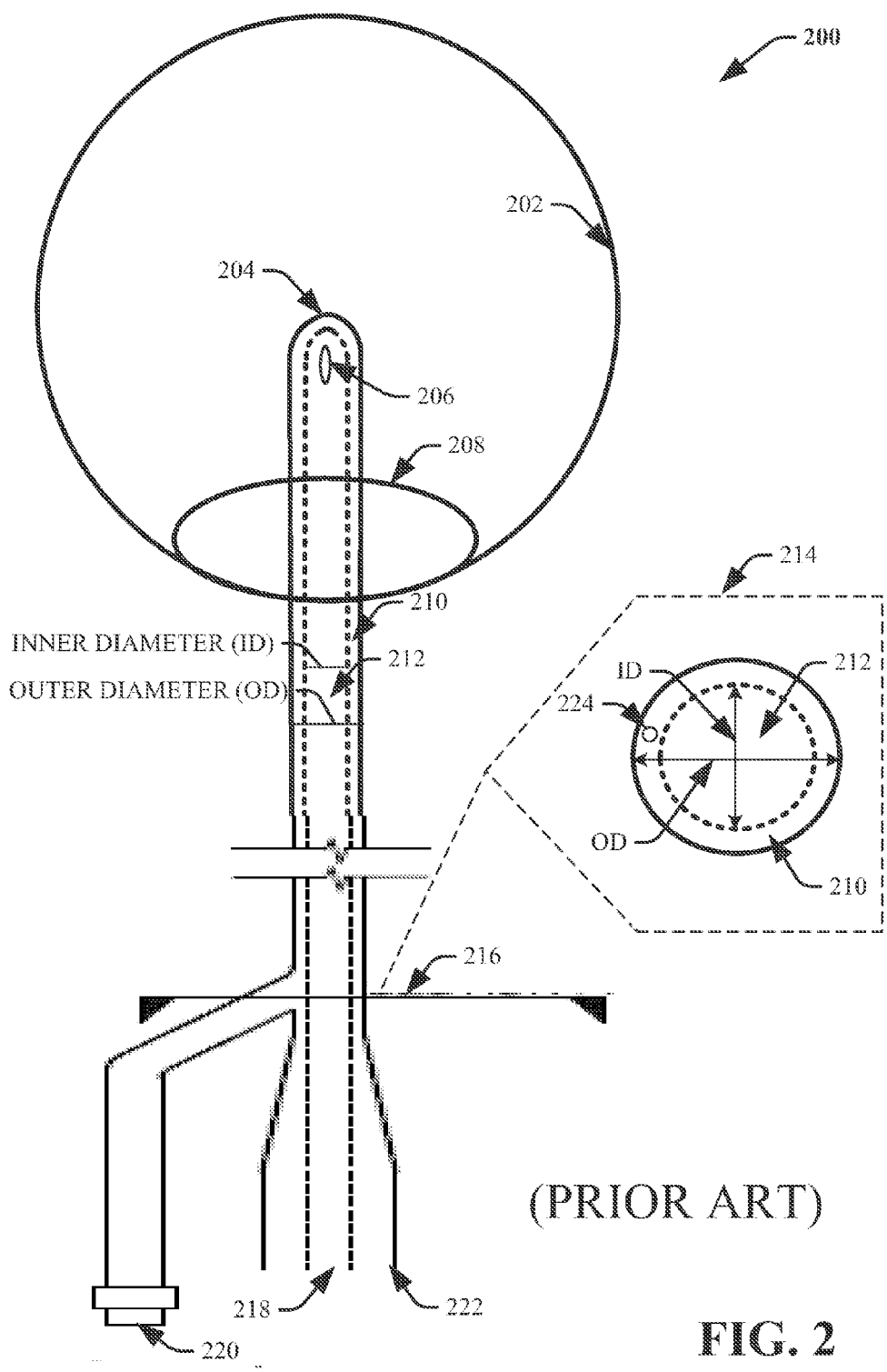
FIG. 2 presents an example conventional Foley catheter in accordance with various aspects and embodiments described herein.

FIG. 2 depicts an example conventional Foley catheter 200 positioned with respect to a human bladder 202. A conventional Foley catheter 200 consists of a long, flexible, cylindrical body or tube that has two separated cylindrical channels, or lumens, running down its length. The outer lumen 210 has a valve 220 on the outer or distal end and connects to a balloon 208 located at the inner or proximal end 204 of the catheter. The outer or distal end 222 of the catheter is provided outside of the body when the catheter is inserted into the urinary tract. The balloon 208 lies on the inner surface of the bladder 202 wall. The balloon 208 is inflated via the valve 220 with sterile water when it lies inside the bladder in order to stop it from slipping out.

The inner lumen 212 runs through middle of the catheter body or tube. A dashed line is used to represent the wall of the inner lumen 212 to indicate that it is located within the catheter body (e.g., surrounded by the outer lumen). The inner lumen 212 is open at both ends to allow urine to drain out into a collection bag (not shown). In particular, the inner lumen includes one opening 206 at the inner or proximal end 204 of the catheter and an opening 218 located on the outer or distal end 222 of the catheter.

Call out box 214 provides a cross-sectional view of conventional Foley catheter 200 taken along line 216. As seen in call out box 214, the inner lumen 212 has a circular shape (represented by the dashed circle) with an inter diameter (ID) that defines the size of the inner lumen. The inner lumen 212 is a hollow, cylindrical, tube provided within the center of the catheter body. The outer lumen 210 consists of a channel formed around the outside of the inner lumen. The outer lumen channel is defined by the space between the wall of the outer lumen (the solid line circle) and the wall of the inner lumen (the dashed line circle). The size of the outer lumen is defined by the diameter of the outer lumen, identified as outer diameter (OD). A single filling channel 224 is also provided within the outer lumen 210 that extends through the length of the outer lumen to the balloon 208 to enable filling of the balloon with water or another fluid following insertion into the bladder.

The OD of the outer lumen 210 of the conventional Foley catheter 200 indicates the size of the catheter. In particular, the size of conventional Foley catheter 200 is equal to (or substantially equal to) the OD along its primary length (e.g., the portion of the catheter above line 216). As seen in FIG. 2, the OD of the conventional Foley catheter 200 does not vary along its primary length. Conventional Foley catheters are available in various sizes. The relative size of a Foley catheter is described using French units (Fr), where 1 Fr is equivalent to 0.33 mm=0.013"=1/77" of diameter. The most common sizes are 10 Fr to 28 Fr, wherein the size refers to the OD of its primary length.

Figure 3:
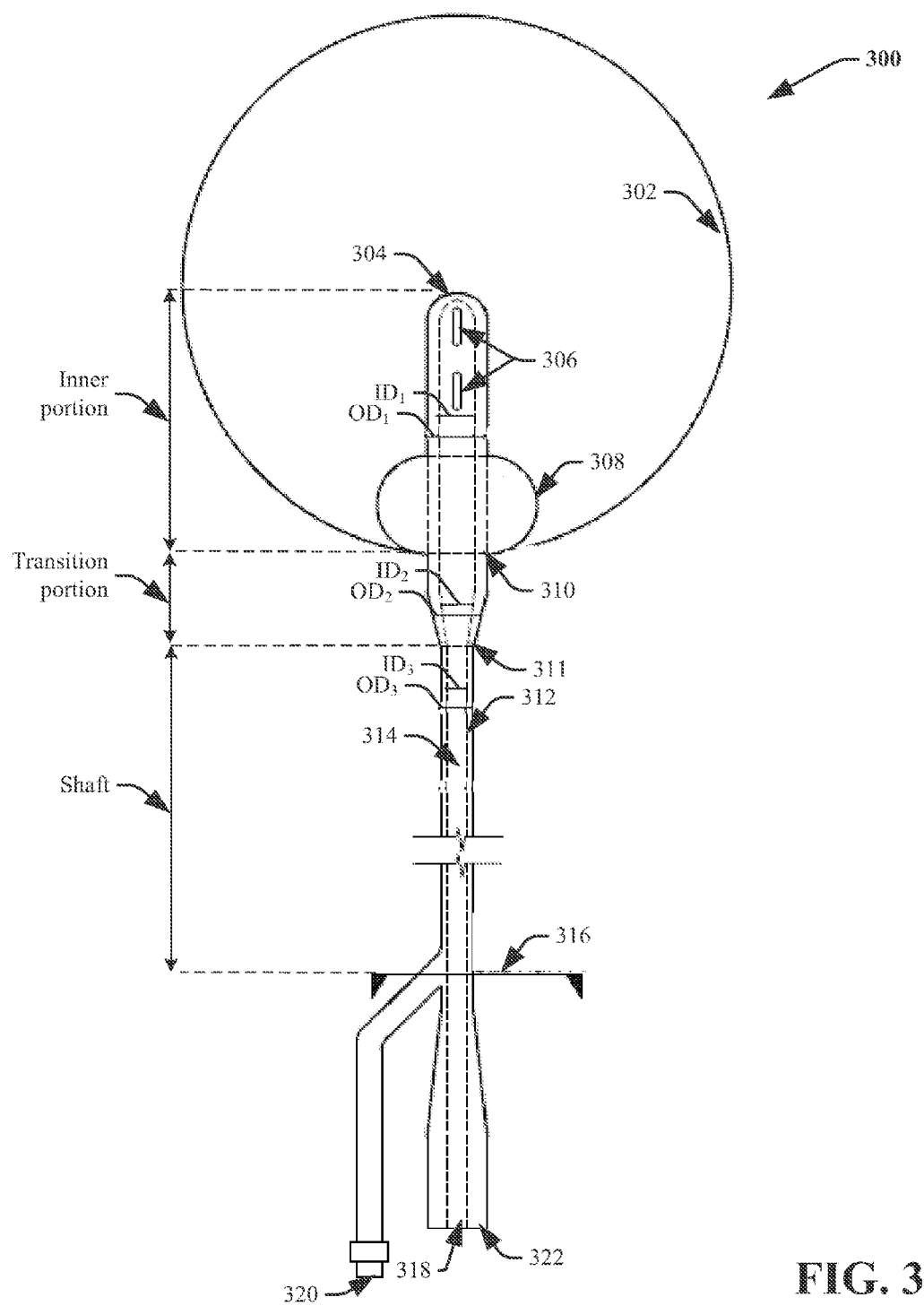
FIG. 3 presents an exemplary tapered catheter in accordance with various aspects and embodiments described herein.

FIG. 3 depicts an example tapered catheter 300 positioned with respect to a human bladder 302 in accordance with various aspects and embodiments disclosed herein. Unlike the body of the conventional Foley catheter 200, the cylindrical body of the subject tapered catheter 300 has varying diameters that decrease or taper from a larger diameter at the proximal or inner end 304 of the catheter to a smaller diameter at the outer or distal end 322 of the catheter. By employing a tapered structure, the subject catheter capitalizes on the benefits of catheters having only a relatively small diameter and catheters having only a relatively large diameter (e.g., relative to the median diameter conventional catheter diameter of about 19 Fr), while minimizing the drawbacks of catheters having only a relatively small diameter and catheters having only a relatively large diameter. Repetitive description of like elements employed in various catheters and/or techniques associated with usage of the various catheters is omitted for sake of brevity.

Similar to the conventional Foley catheter 200, tapered catheter 300 consists of a long, flexible, cylindrical, body or tube that has at least two separated channels, or lumens, running down its length, an outer lumen 312 and an inner lumen 314. The outer lumen 312 has a valve 320 on the outer or distal end and connects to a balloon 308 located at the inner or proximal end 304 of the catheter. The outer or distal end of the catheter 322 is provided outside of the body when the catheter is inserted into the urinary tract. The balloon 308 lies on the inner surface of the bladder 302 wall. The balloon 308 is inflated via valve 320 with sterile water when it lies inside the bladder in order to stop it from slipping out.

The inner lumen 314 runs through middle of the cylindrical catheter body or tube. A dashed line is used to represent the wall of the inner lumen 314 to indicate that it is located in the middle of the cylindrical catheter body (e.g., surrounded by the outer lumen). The inner lumen 314 is open at both ends to allow urine to drain out into a collection bag provided at opening 318 (not shown). In particular, the inner lumen 314 includes one or more openings 306 at the inner or proximal end 304 of the catheter and an opening 318 located on the outer or distal end. It is specifically noted that unlike the conventional catheter 200, the subject tapered catheter can include more than one opening 306 at the proximal end through which urine (and other secretions) are collected. For example, the subject catheter 300 is depicted with two openings. However it should be appreciated that any number N of openings can be employed at the proximal end of the catheter.

Tapered catheter 300 is divided into three parts, an inner portion, a transition portion, and a primary shaft. Each of the three parts respectively have a different outer diameters (ODs) for the outer lumen 312 and inner diameters (IDs) for the inner lumen 314. In particular, the inner portion has an $ID_1$ and $OD_1$, the transition portion has at least an $ID_2$ and $OD_2$, and the primary shaft has an $ID_3$ and $OD_3$. The ODs of the outer lumen for the three parts of tapered catheter 300 have the following relationship: $OD_1 > OD_2 > OD_3$. In addition, the inner diameters of the inner lumens of the three parts of tapered catheter 300 have the following relationship: $ID_1 > ID_2 > ID_3$.

Regarding the relationship between $OD_1$ and $OD_2$, in an aspect, $OD_2$ is less than or equal to 90% of $OD_1$. In another aspect, $OD_2$ is less than or equal to 80% of $OD_1$. In another aspect $OD_2$ is less than or equal to 70% of $OD_1$. In another aspect $OD_2$ is less than or equal to 60% of $OD_1$. In yet another aspect $OD_2$ is less than or equal to 51% of $OD_1$. Regarding the relationship between $OD_1$ and $OD_3$, in an aspect, $OD_3$ is less than or equal to 90% of $OD_1$. In another aspect, $OD_3$ is less than or equal to 80% of $OD_1$. In another aspect $OD_3$ is less than or equal to 70% of $OD_1$. In another aspect $OD_3$ is less than or equal to 60% of $OD_1$. In yet another aspect $OD_3$ is less than or equal to 51% of $OD_1$.

The respective lengths of the inner portion, transition portion, and primary shaft can vary. In another aspect, the inner portion has a length of about 5.0 centimeters (cm) to about 20.0 cm, the transition portion has a length of about 1.0 to 5.0 cm, and the primary shaft has a length of about 10.0 to 50.0 cm. In another aspect, the inner portion has a length of about 5.0 cm to about 15.0 cm, the transition portion has a length of about 1.0 to 2.0 cm, and the primary shaft has a length of about 20.0 to 30.0 cm.

In an exemplary embodiment, the transition portion has a funnel or cone shape, wherein the diameter of the proximal end 310 of the transition portion is larger than the diameter of the distal end 311 of the transition portion. According to this embodiment, the $OD_2$ of the transition portion varies by slowly descending from a larger diameter at the proximal end 310 to a smaller diameter at the distal end 311. In an aspect, the $OD_2$ of the transition portion that is adjacent to the body of the catheter at the inner portion (e.g., at proximal end 310) is the same as $OD_1$, and the $OD_2$ of the transition portion that is adjacent to the shaft (e.g., at distal end 311) is the same as $OD_3$. In aspect, the $ID_2$ of the transition portion also mirrors the $OD_2$ and varies by slowly descending from a larger diameter at the proximal end 310 to a smaller diameter at the distal end 311. In another aspect, the $ID_2$ of the transition portion is constant.

The inner portion of catheter 300 has openings 306 to allow urine in the bladder to flow into the catheter. Since the inner portion of the catheter 300 is configured to be situated inside of the bladder when the catheter is inserted, the size of the inner portion can be increased to facilitate optimized urine collection and to minimize the possibility of blockage. The bladder 302 has a large diameter and thus the portion of the catheter located therein can be increased without causing additional irritation of the bladder. Therefore, the size (e.g., $ID_1$ and $OD_1$) can be increased significantly over that of the size of the conventional Foley catheter. In an aspect, the inner portion of catheter 300 has an $OD_1$ of about 28.0 Fr to about 14.0 Fr. In another aspect the inner portion has an $OD_1$ of about 28.0 Fr to about 20.0 Fr. Still in yet another aspect, the inner portion as a $OD_1$ of about 24.0 Fr to about 28.0 Fr. The sizing table provided in Appendix A provides additional example sizes for the inner portion of catheter 300 in accordance with various aspects and embodiments.

The transition portion of tapered catheter 300 is a segment inferior to the bladder 302 that is designed to provide additional buttress to prevent urinary leakage around the catheter between the bladder 302 and the urethra. In particular, when the catheter 300 is inserted into the urinary track, the transition portion is configured to be positioned adjacent to the outer wall of the bladder 302. The length of the transition portion can vary. In an aspect, the length and diameter of the transition portion is selected to be a minimal length and diameter so that it provides a least amount of irritation to the urethral mucosa due to its size being larger than that of the shaft while still providing the additional buttress to prevent urinary leakage. In an aspect, the length of the transition portion is between about 1.0 and 4.0 cm. In another aspect, the length of the transition portion is between about 1.0 and 2.0 cm. In an aspect, the transition portion $OD_2$ has a tapering diameter from about 28.0 Fr at end 310 to about 10.0 Fr at end 311 with a median diameter of 14.0 Fr. In another aspect, the transition portion $OD_2$ has a tapering diameter from about 24.0 Fr at end 310 to about 12.0 Fr at end 311 with a median diameter of 18.0 Fr. In yet another aspect, the transition portion $OD_2$ has a tapering diameter from about 20.0 Fr at end 310 to about 14.0 Fr at end 311 with a median diameter of 17.0 Fr. The sizing table provided in Appendix A provides additional example sizes for the transition portion of catheter 300 in accordance with various aspects and embodiments described herein.

The transition portion of catheter 300 provides for a transition from the larger diameter of the inner portion lumen located in the bladder to the smaller diameter of the primary shaft lumen. The primary shaft is the part of the catheter that connects the transition portion to distal end 322 or outside portion of the catheter that includes the urine collection bag (not shown) and valve 320. In an aspect, the primary shaft portion of the catheter is the longest portion of the catheter and is located within the majority of the urethra when catheter 300 is inserted (as compared to the transition portion). The length of the primary shaft can vary. The primary shaft portion is designed to have the smallest OD and ID possible that still allows urine to pass. In particular, $OD_3$ can be significantly smaller than $OD_2$ and $OD_1$. In an aspect, the primary shaft has an $OD_3$ of about 10.0 Fr to about 16.0 Fr. In another aspect, the primary shaft has an $OD_3$ of about 12.0 Fr to about 15.0 Fr. In yet another aspect, the primary shaft has an $OD_3$ of about 13.0 Fr to about 14.0 Fr. The sizing table provided in Appendix A provides additional example sizes for the primary shaft of catheter 300 in accordance with various aspects and embodiments. By employing a primary shaft with a smaller diameter, irritation of the urethral mucosa can be significantly reduced, thus minimizing mucosal injury, enhancing patient comfort, and ultimately decreasing susceptibility to bacterial infection.

Cather 300 can be formed using various materials that provide biocompatibility, including but not limited to silicones, polyethylene terephthalate (PET), and latex rubber. In an aspect, the different parts (e.g., the inner portion, the transition portion, the shaft, the inner lumen, the outer lumen, etc.) of catheter 300 are made of the same material. In another aspect, one or more of the different parts are formed with different materials. In an aspect, catheter 300 is coated on the outer and/or the inner lumen to prevent bacterial overgrowth. For example, catheter 300 can be coated on the inside and outside lumen walls with a biomimetic surface to prevent bacterial or other microbial growth. In another example, the surfaces of catheter 300 are impregnated with antibiotics, antibacterial or coated with biocompatible materials that prevent bacterial overgrowth, such as silver or copper.

In addition, the inside wall of the inner lumen 314 can be coated with a material that has low friction to enhance urine flow. This material can include but is not limited to: plastic, PET, a naturally occurring latex, or synthetic latex material. In another aspect the outer surface of the catheter 300 is coated with a material designed to reduce friction so that the catheter can be inserted easily without undue force or trauma to the urethra or the bladder or any other body part. In another aspect, the catheter 300 is coated on the outer surface with a material that enhances mucosal growth.

Figure 4:
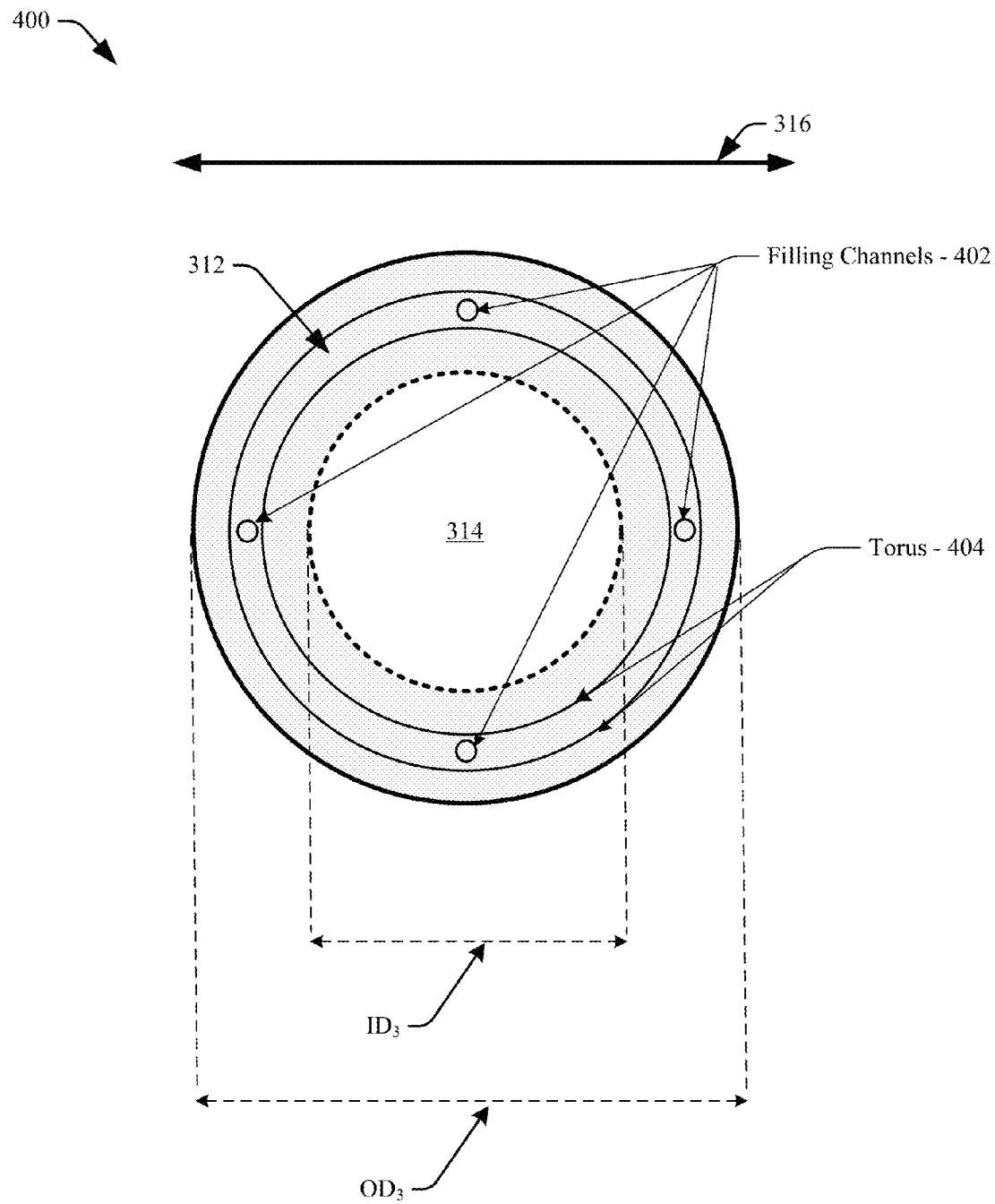
FIG. 4 presents a cross-sectional view of an exemplary tapered catheter in accordance with various aspects and embodiments described herein.

FIG. 4 presents an enlarged cross-sectional view 400 of tapered catheter 300 taken along line 316 in accordance with various aspects and embodiments described herein. Repetitive description of like elements employed in various catheters and/or techniques associated with usage of the various catheters is omitted for sake of brevity.

The cross-section of catheter 300 is similar in part to that of the cross-section of catheter 200 depicted in call out box 214 in that the inner lumen 314 has a circular shape (represented by the dashed circle) with an inner diameter ($ID_3$) that defines the size of the inner lumen. The inner lumen 314 is also a hollow, cylindrical, tube provided within the center of the catheter body. In addition, the outer lumen 312 consists of a channel formed around the outside of the inner lumen. The outer lumen channel is defined by the space between the outer wall of the outer lumen (represented by the solid circle) and the wall of the inner lumen (the dashed circle) and depicted in a light grey color to differentiate it from the inner lumen 314. The size of the outer lumen is defined by $OD_3$.

Unlike the conventional catheter 200, the outer lumen 312 of catheter 300 includes a torus 404 provided within the body of the outer lumen at or near the portion of catheter 300 represented by line 316. The torus 404 includes a plurality of filling channels 402 configured to extend throughout the length of the outer lumen and connect to the balloon provided at the end thereof. These filling channels are used to fill the balloon with sterile water when inserted into the bladder. In an exemplary embodiment, the torus includes four channels spaced substantially evenly around the circumference of the torus. With this configuration, when the catheter is inserted into the urinary tract and pressure against one side of the catheter causes one of the filling channels to close, a filling channel on the opposite side that is not affected by the pressure can still facilitate filling the balloon. It should be appreciated that although four filling channels 402 are depicted, a number of filling channels can be employed. However, it is preferred that catheter 300 includes at least two or more filling channels provided in different regions of the torus 404.

Figure 5:
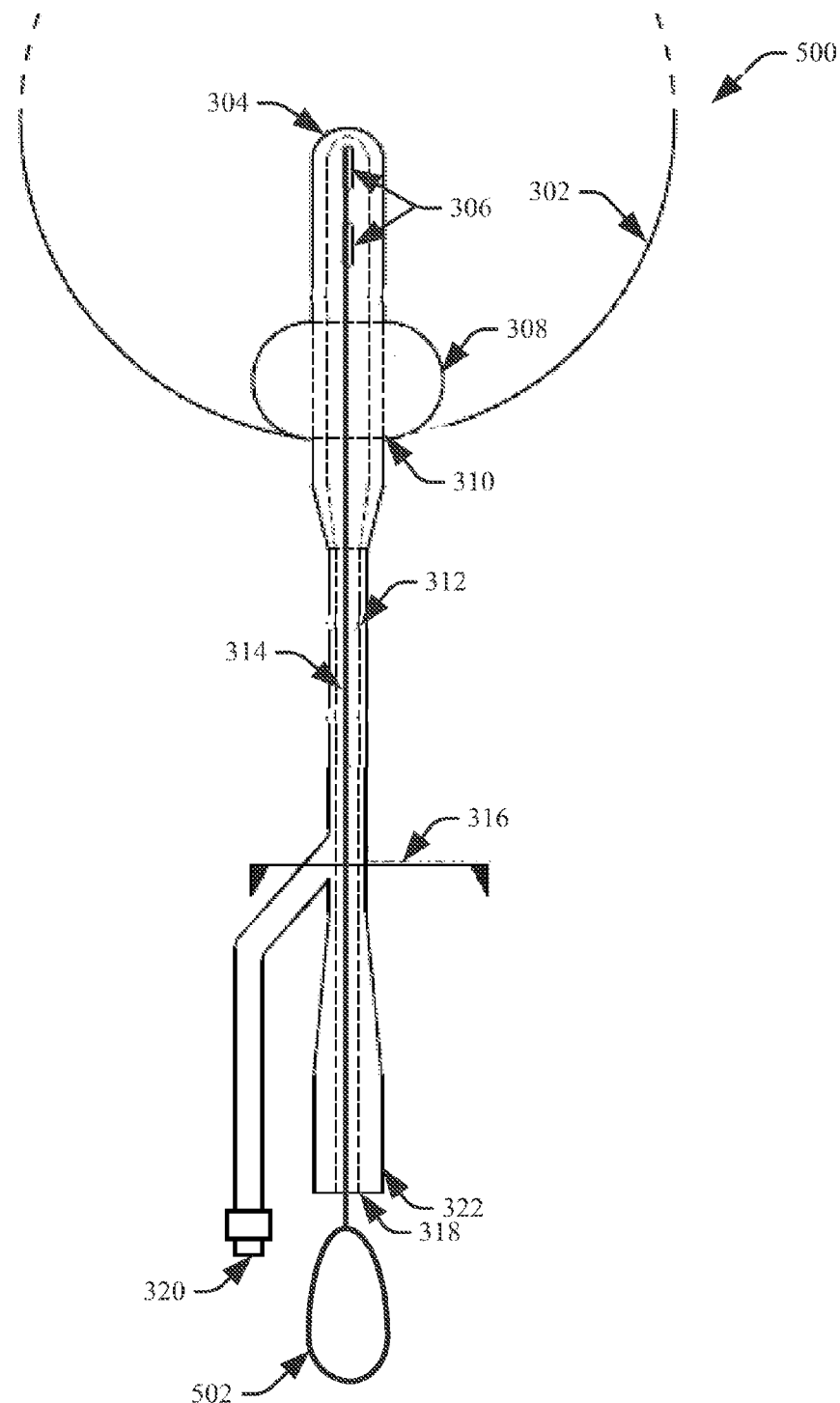
FIG. 5 presents another exemplary tapered catheter having an introducer in accordance with various aspects and embodiments described herein.

FIG. 5 depicts another example tapered catheter 500 positioned with respect to a human bladder 302 in accordance with various aspects and embodiments disclosed herein. Catheter 500 can include same or similar features and functionality as catheter 300 (and vice versa). Repetitive description of like elements employed in various catheters and/or techniques associated with usage of the various catheters is omitted for sake of brevity.

The rigidity of the subject tapered catheters (e.g., catheters 300 and 500) can vary to facilitate smooth insertion of the catheter into the urinary tract. For example, one or more portions of catheter 500 can include a flexible tube. The flexibility of the tube can vary depending on the material employed to form the tube and the thickness of the tube. In another example, one or more portions of catheter (e.g., the inner portion, the transition portion, the external components below line 316, etc.) can include a rigid or non-flexible material.

In an aspect, when at least a portion of catheter 500 includes a flexible tube, an introducer 502 can be employed to facilitate insertion of the catheter into the urinary tract. The introducer 502 is configured to insert into the inner lumen 314 through opening 318 to enhance the radial and axial rigidity of the catheter body. The introducer can be formed with various materials that allow the introducer to have a smaller diameter than that of the inner lumen while providing sufficient rigidity to facilitate insertion. In an aspect, the introducer is formed from of a metal or hard plastic material. The introducer is removed from the body once the catheter has been successfully advanced into the bladder. In an aspect, the introducer 502 is designed such that it can be inserted into the inner catheter lumen 314 and reaches the tip without extending beyond the tip 304 or providing any injury to the tip of the catheter. The introducer is designed so that it does not obstruct urinary flow and will allow urine to flow once the catheter is past the bladder neck and thus serving as a marker of adequate catheter advancement.

Figure 6:
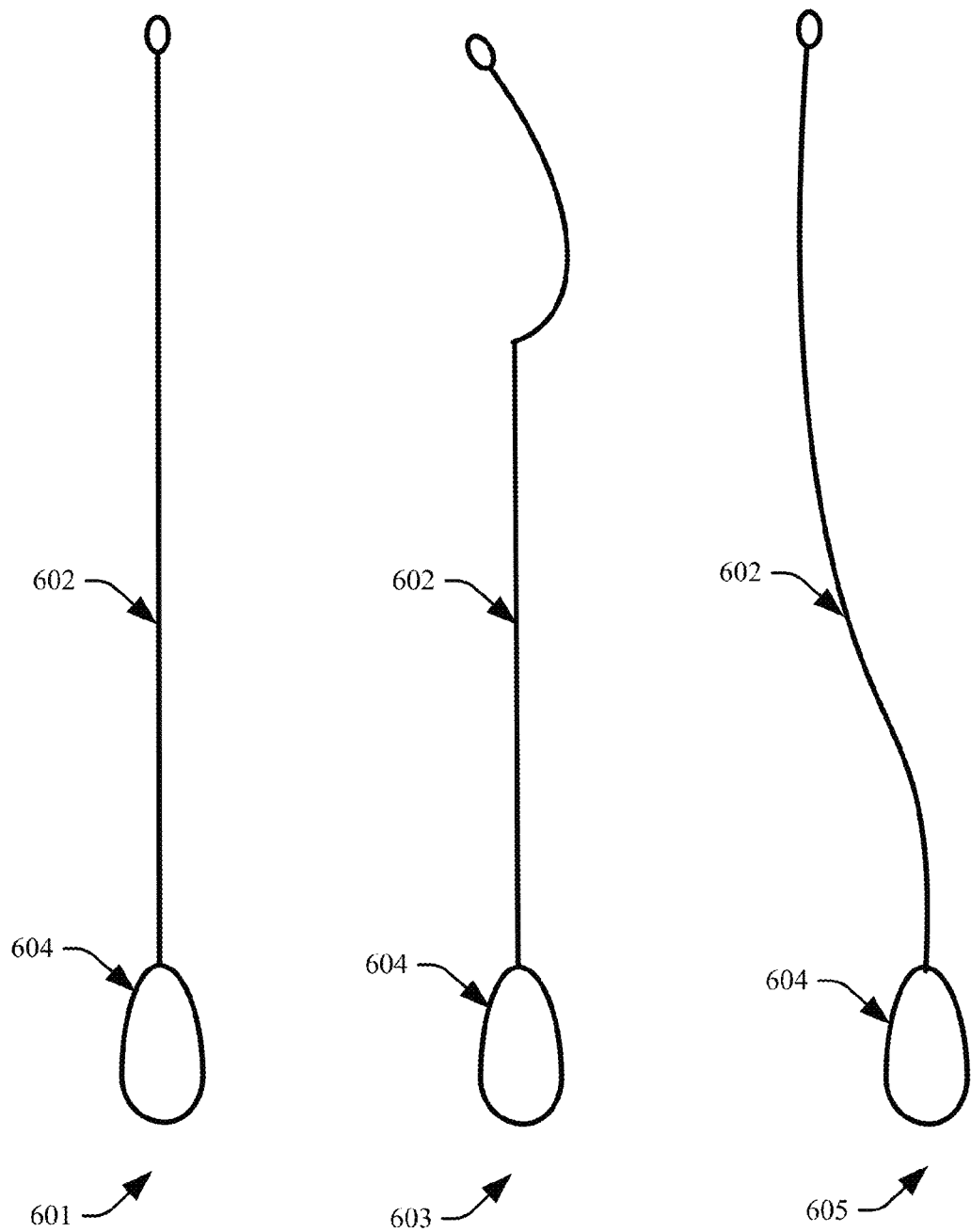
FIG. 6 provide exemplary introducers for use with a tapered catheter in accordance with various aspects and embodiments described herein.

FIG. 6 present example introducers 601, 603 and 605 that can be employed in association with the subject tapered catheter in accordance with various aspects and embodiments disclosed herein. Repetitive description of like elements employed in various catheters and/or techniques associated with usage of the various catheters is omitted for sake of brevity.

Introducers employed in association with the subject tapered catheter can have various configurations. Each of the introducers can have an elongated stem 602 and a hook or handle 604 to facilitate holding the introducer. When inserted into the inner lumen of the subject catheters, the body of the catheter takes on the shape of the introducer. The elongated stems 602 can have various degrees of flexibility and rigidity. In one aspect, the elongated stem 602 is substantially straight, as demonstrated by example introducer 601. In another aspect, the elongated stem 602 has a curve or hook formation at one end, as demonstrated by example introducer 603. Still in yet another aspect, the elongated stem 602 is slighted curved in an S formation, as demonstrated by example introducer 605.

FIGS. 7A-7D present yet another example tapered catheter 700 in accordance with various aspects and embodiments disclosed herein. Catheter 700 can includes same or similar features and functionality of catheters 300 and 500 with the addition of introducer 704 and sanitary bag 702. It should be appreciated that only the outer or distal end 322 of catheter 700, (e.g., the portion of catheter 300 around line 316) is depicted merely for exemplary purposes. The missing portion of the catheter 700 provided above line 316 can substantially mimic that of catheter 300 or 500. Repetitive description of like elements employed in various catheters and/or techniques associated with usage of the various catheters is omitted for sake of brevity.

Figure 7A:
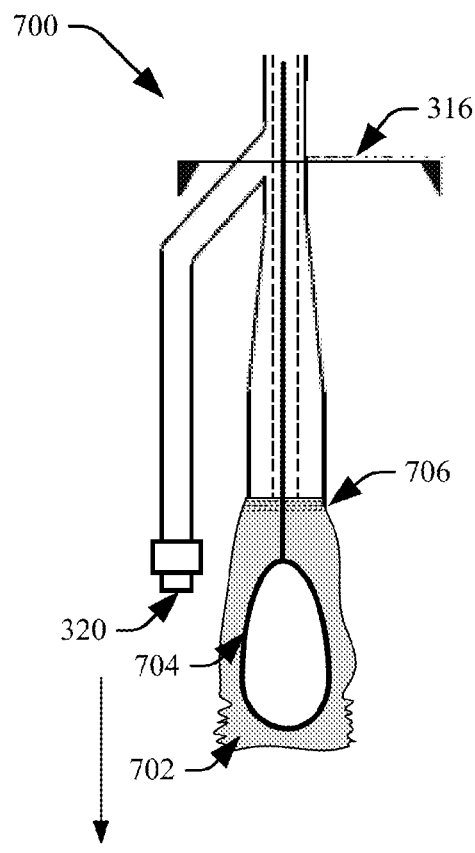
FIGS. 7A-7D presents other examples of tapered catheter in accordance with various aspects and embodiments disclosed herein.

FIG. 7A presents an example catheter 700 in a formation prior to insertion and or following insertion into the urinary track. Introducer 704 is located within the inner lumen of the catheter to facilitate its insertion into the urinary tract, as discussed above. Introducer 704 is provided with flexible and expandable sanitary bag 702. In an aspect, the sanitary bag is formed via a thin plastic or polymer. The sanitary bag 702 is further attached to the base of the catheter 700 via a releasable seal 706. The introducer 704 is sterilized within the sanitary bag 704. The introducer 702 is provided within the sealed sanitary bag so that it can remain sterile while it is used to facilitate insertion of the catheter 700 into the urinary tract. After the catheter 700 is introduced into the urinary tract, the seal 706 can be broken and the introducer 704 can be removed within the sanitary bag 702.

Figure 7B:
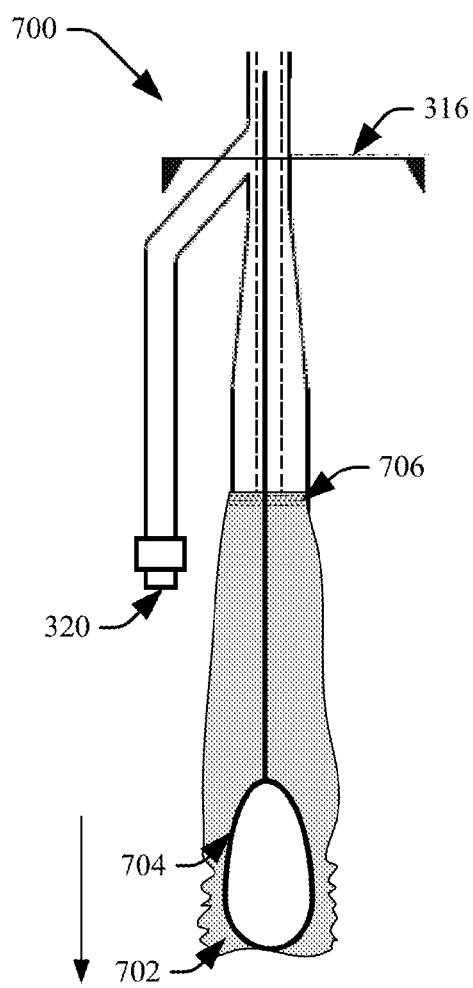

FIG. 7B depicts catheter 700 as the introducer 704 is removed. In particular, a user can grip the introducer by the handle (e.g., the loop) which is inside of the sanitary bag and slowly pull the introducer out. As the introducer 704 is pulled out, the sanitary bag expands (e.g., in an accordion fashion) or extends with the introducer. In an aspect, the seal 706 is not released until the introducer has been fully removed (e.g., the tip of the introducer has cleared the base of the catheter).

Figure 7C:
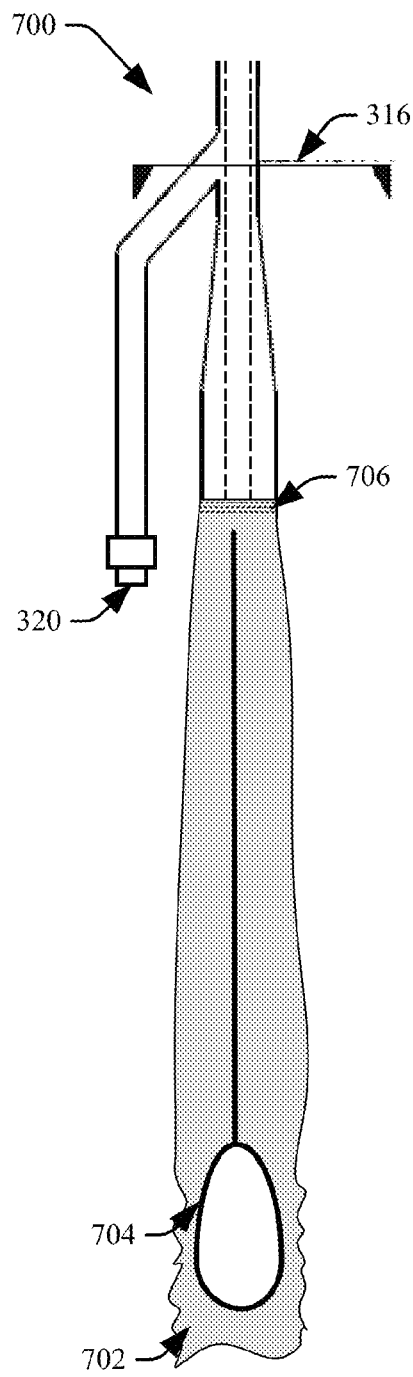

FIG. 7C further depicts catheter 700 as the introducer 704 is removed. In FIG. 7C, introducer has been fully removed such that the tip of the introducer has cleared the base of the catheter 700. In other words, the introducer is no longer located within the body of the catheter, (e.g., within the inner lumen). At this time, the seal 706 can be broken or released.

Figure 7D:
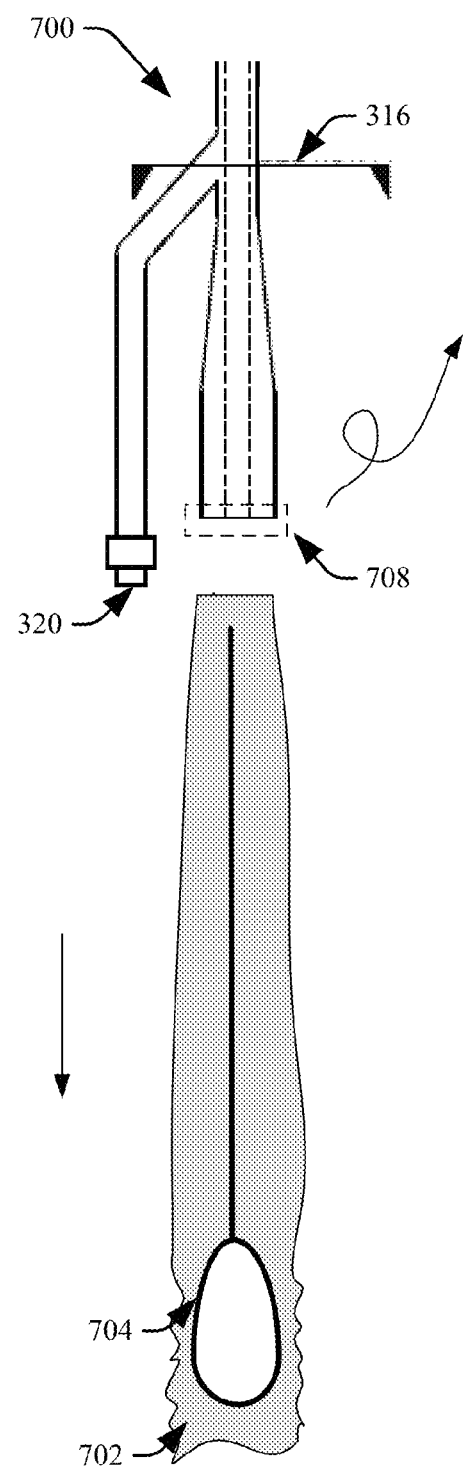

FIG. 7D demonstrates breaking of the seal and release of the introducer 704 while it remains inside the sanitary bag 702. In particular, as seen in FIG. 7D, the seal is broken, (as indicted by dashed box 708), and the introducer 704 and sanitary bag 702 are no longer attached to the catheter 700.

Figure 8:
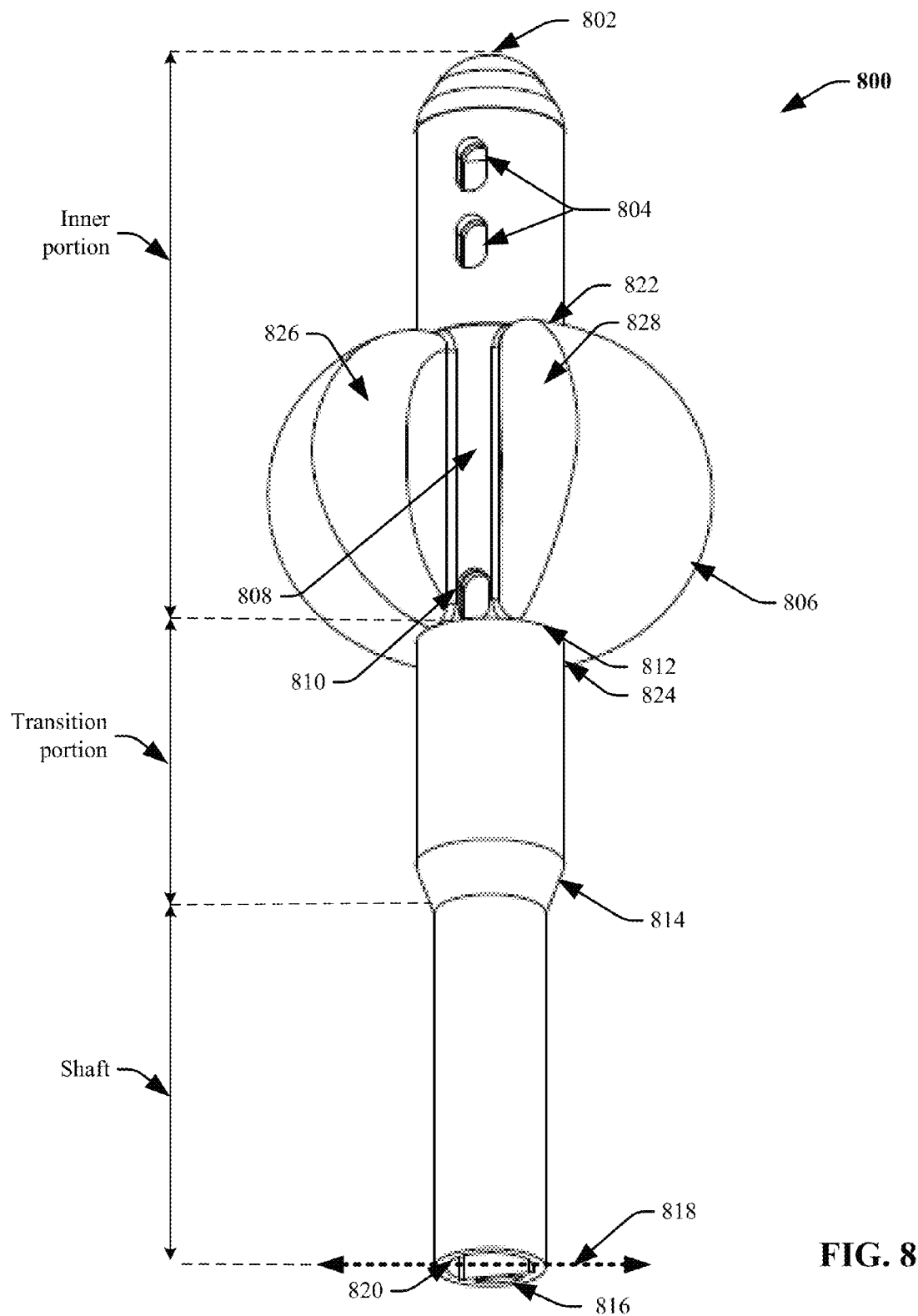
FIG. 8 presents a three dimensional view of another example tapered catheter having a balloon with a channel and a lower drainage hole provided within the channel in accordance with various aspects and embodiments described herein.

FIG. 8 depicts a three dimensional view of the upper portion of another example tapered catheter 800 in accordance with various aspects and embodiments disclosed herein. Similar to example catheters 300 and 500 (and the like), catheter 800 has a cylindrical body with varying diameters that decrease or tapper from a larger diameter at the proximal or inner end 802 of the catheter to a smaller diameter at the outer or distal end (not shown) of the catheter. For example, catheter 800 includes an inner portion, a transition zone and a shaft, wherein at least the OD of the shaft is smaller than that of the transition portion and the inner portion. Also similar to catheters 300 and 500, a lower part 814 of the inner portion that connects to the shaft has varying diameters that form a funnel shape.

It should be appreciated that although the lower portion of catheter 800 (corresponding to the portion of the catheter that continues past dashed line 818) is not depicted, this portion of the catheter can include various conventional catheter configurations and components, such as those depicted below dashed line 316 in FIG. 3. For example, the lower portion of catheter 800 can include additional shaft length and catheter components that are positioned outside of the body when the catheter is inserted into the urinary tract (e.g., a balloon filling valve, additional valves, a collection bag, etc.). The dimensions and materials of the various components of catheter 800, including the inner portion, the transition portion, the shaft, the inner lumen, the outer lumen, etc., can correspond to those described for same or similar components of catheter 300. Repetitive description of like elements employed in various catheters and/or techniques associated with usage of the various catheters is omitted for sake of brevity.

Similar to catheters 300 and 500, the inner portion of catheter 800 includes a balloon located at the base of the inner portion 812 (e.g., the portion of the catheter body at the boundary between the inner portion and the transition portion). The balloon is connected to channel or lumen 816 that extends through the catheter body and allows for filling of the balloon with gas or sterile water. This balloon filling lumen or channel is referred to herein as the outer lumen 816. After the catheter is inserted into the urinary tract and the inner portion is located within the bladder, the balloon is filled with gas or sterile water via the outer lumen 816. When the balloon is filled or inflated (as it is depicted in FIG. 8), the balloon rests within the bladder and serves to prevent the catheter from slipping out of the bladder. For example, as depicted in FIG. 1, the balloon 108 can rest on the lower inner lining or wall of the bladder around the urethra opening in the bladder. One or more drainage holes or openings 804 and/or 810 are provided on the body of the catheter which connect to a second lumen or channel 820 that extends through the body of the catheter. This second lumen or channel 820 is referred to herein as the inner lumen. These drainage holes or openings 804 and/or 810 allow for the draining of urine from the bladder through the drainage holes into the inner lumen 820 and eventually excreted outside of the body (e.g., into a urine filling bag connected to the inner lumen outside of the body, not shown).

In an aspect, as depicted in FIG. 8, catheter 800 can include at least two upper drainage holes 804 located on the catheter body above the balloon 806 (e.g., between the top surface 822 of the balloon and the proximal end 802 or tip of the catheter body). It should be appreciated however that although two upper drainage holes 804 are depicted, catheter 800 can include any number N (where N is an integer) of upper drainage holes located at various positions around the circumference of the catheter body (e.g., on the same side as depicted, on opposite sides, etc.). In another aspect, catheter 800 does not include any upper drainage holes.

Catheter 800 particularly exemplifies a unique design for the balloon 806 of the inner portion of the catheter body that allows for inclusion of at least one lower drainage hole 810 on the catheter body below and/or surrounded by at least a portion of the balloon 806 (e.g., below the top surface 822 of the balloon). This lower filling prevents and/or alleviates complications associated with an underactive bladder condition by allowing for complete emptying of urine in the bladder. In particular, depending on the position of the patient wearing the catheter (e.g., standing, sitting, laying, etc.) urine may level in the bladder below the upper drainage holes and thus not flow into the upper drainage holes and remain in the bladder.

For example, FIG. 9 demonstrates two scenarios wherein a catheter without a lower drainage hole is shown within the bladder 902 having urine 906 remaining therein. In scenario 900, the balloon 806 rests on the lower inner wall 904 of the bladder. Urine 906 (as indicated in gray) remains in the bladder around the balloon because it does not reach the upper drainage holes 804. In scenario 901, the catheter body and attached balloon has shifted upwards a bit from the lower inner wall 904 of the bladder (e.g., in response to movement of the patient) creating a space 908 between the balloon and the lower inner wall 904 of the bladder. In this scenario, urine 906 remains in the bladder around the balloon and within the space 908 because it does not reach the upper drainage holes 804.

With reference back to FIG. 8, catheter 800 includes at least one lower drainage hole 810 at or near the base 812 of the inner portion of the catheter body to allow for complete emptying of the bladder to prevent the scenarios depicted in FIG. 9 and other similar scenarios. The lower drainage hole is located below and/or surrounded by at least a portion of the balloon 806. For example, lower drainage hole 810 is located between the top surface 822 and a lower surface 824 of the balloon 806 and between two side surfaces of the balloon 826 and 828. In order to include this lower drainage hole the balloon is formed with an irregular shape that includes an opening or space between the body of the balloon and the body of the inner portion of the catheter for the lower drainage hole. In an aspect, this opening is in the form of a channel 808 that extends from the top surface 822 of the balloon to the bottom surface 824 of the balloon. For example, as seen in FIG. 8, the balloon is shaped as a sphere with a slice cut out such that a channel 808 is established along the length of the inner portion of the catheter between the upper 822 and lower 824 surfaces of the balloon and between two side surfaces 826 and 828 of the balloon. The lower drainage hole 810 is provided at or near the base of the channel 808 (e.g., a the boundary 812 between the inner portion and the transition portion). With this configuration, the balloon resembles an orange with a slice removed and has a what is referred to herein as a C shape.

It should be appreciated that the shape and design of the balloon 806 can vary and can be adapted to allow for additional lower drainage holes at the based on the inner portion. For example, the balloon could be divided into several separate hemispherical sections (slices) of equal size, wherein channels are respectively established between each section and a lower drainage hole is provided at the base of each channel.

Catheter 800 also depicts an example inner and outer lumen configuration that is different from that of catheters 300 and 500. In particular, rather than employing an outer lumen that forms a cylindrical ring around a cylindrical inner lumen (e.g., a tube within a tube) as illustrated by the cross-section of catheter 300 depicted in FIG. 4, catheter 800 includes an inner lumen 820 and an outer lumen 816 formed within a single cylindrical tube by division with a single wall. With this configuration, the outer lumen 816 does not surround or form a ring around the inner lumen 820. The outer lumen 816 extends along a first side of the cylindrical body of the catheter and the inner lumen 820 extends along a second side of the cylindrical body.

The dimensions of the inner lumen 820 and outer lumen 816 can vary. In an aspect, the inner lumen 820 is larger (e.g., has a wider cross-section) than the outer lumen 816 as depicted in FIG. 8. However in other aspects, the outer lumen 816 and the inner lumen 820 can have the same dimensions or the outer lumen can 816 can be larger (e.g., have a wider cross-section) than the inner lumen 820. In an aspect, the rigidity of the outer lumen and the inner lumen is the same. In another aspect, the rigidity of the outer lumen and the inner lumen can vary. For example, the wall(s) of the outer lumen 816 can be formed with a material that is more rigid than a material that forms the wall(s) of the inner lumen 820 or vice versa.

Figure 10:
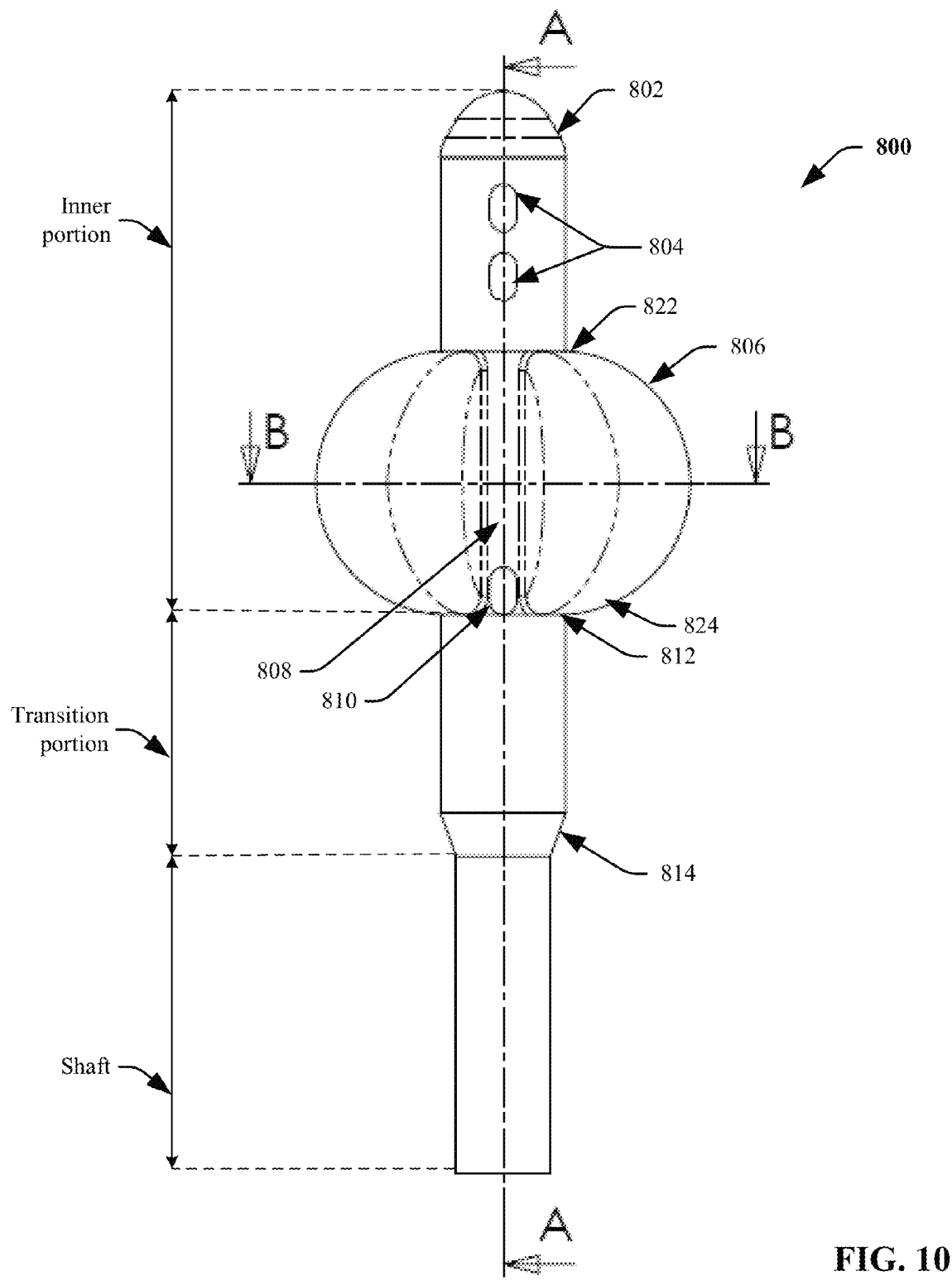
FIG. 10 presents a two dimensional view of the example tapered catheter having the balloon with the channel and the lower drainage hole provided within the channel in accordance with various aspects and embodiments described herein.

FIG. 10 depicts a two dimensional view of the upper portion of example tapered catheter 800 in accordance with various aspects and embodiments disclosed herein. Repetitive description of like elements employed in various catheters and/or techniques associated with usage of the various catheters is omitted for sake of brevity.

Figure 11:
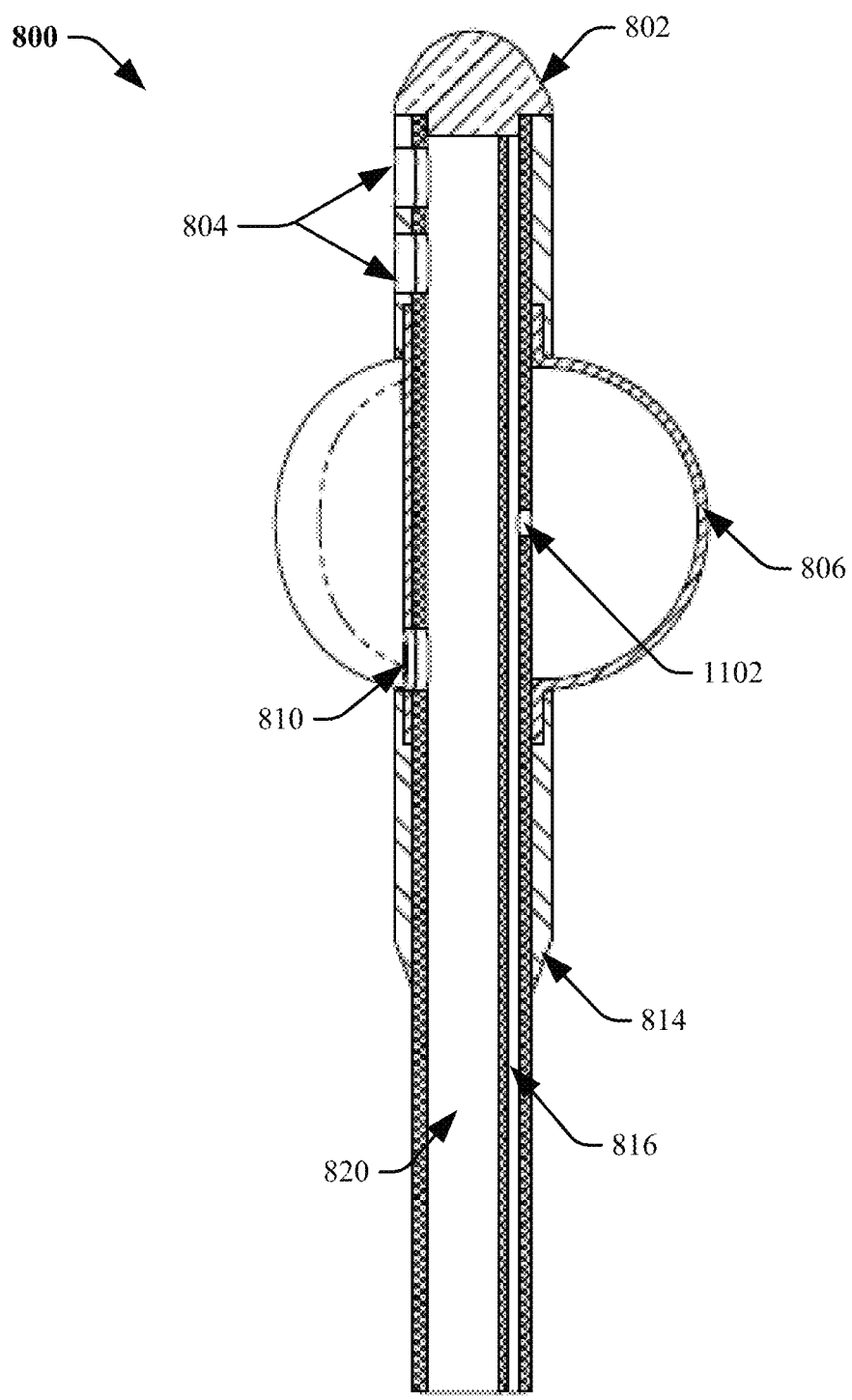
FIG. 11 presents a cross-sectional view of the example tapered catheter having the balloon with the channel and the lower drainage hole provided within the channel in accordance with various aspects and embodiments described herein.

FIG. 11 depicts a cross-sectional view of example tapered catheter 800 taken along axis A-A identified in FIG. 10 in accordance with various aspects and embodiments disclosed herein. Repetitive description of like elements employed in various catheters and/or techniques associated with usage of the various catheters is omitted for sake of brevity.

This cross-sectional view of catheter 800 shows the inner lumen 820 and outer lumen 816 extending throughout the length of the catheter body. The inner lumen 820 is substantially larger (e.g., has a wider cross section) than the outer lumen 816. The upper 804 and lower 810 drainage holes form openings in the inner lumen (e.g., connect to the inner lumen 820 such that urine can flow through the respective drainage holes into the inner lumen 820). A balloon drainage hole 1102 is provided at a junction between the balloon 806 and the outer lumen 816 to allow for inflation or filling of the balloon 806.

Figure 12:
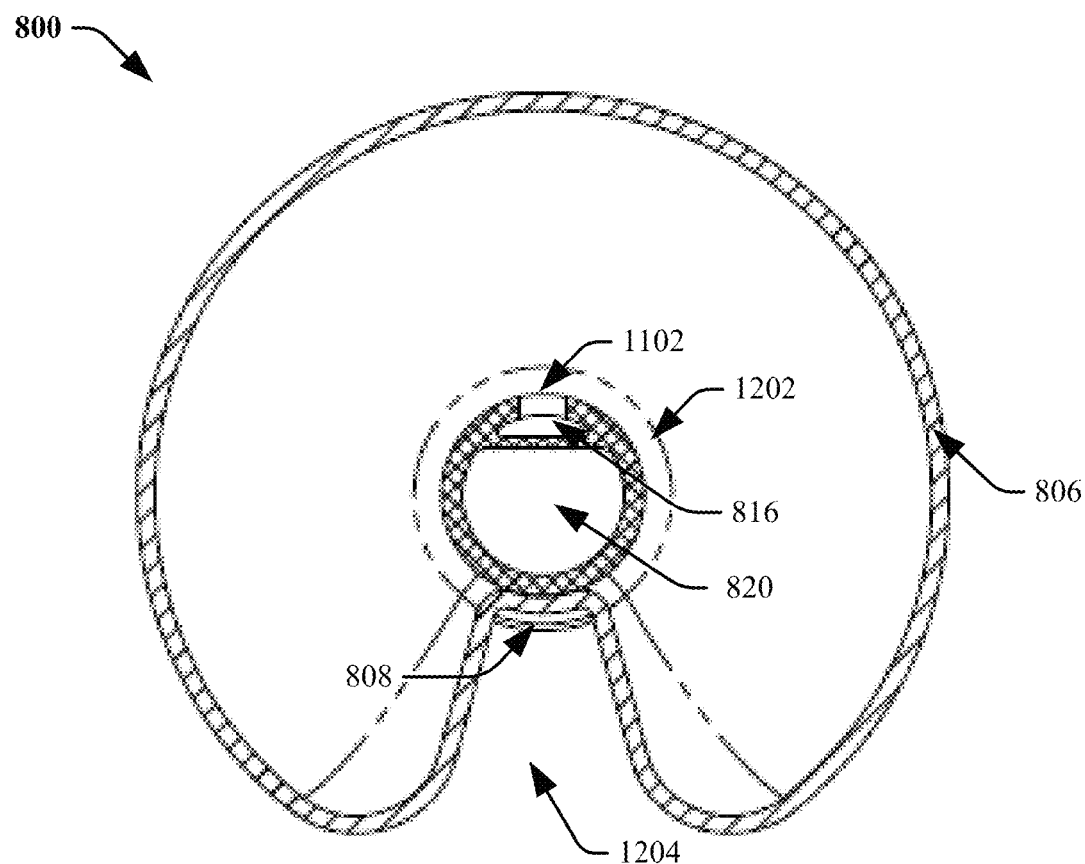
FIG. 12 presents another cross-sectional view of the example tapered catheter having the balloon with the channel and the lower drainage hole provided within the channel in accordance with various aspects and embodiments described herein.

FIG. 12 depicts a cross-sectional view of example tapered catheter 800 taken along axis B-B identified in FIG. 10 in accordance with various aspects and embodiments disclosed herein. Repetitive description of like elements employed in various catheters and/or techniques associated with usage of the various catheters is omitted for sake of brevity.

This cross-sectional view of catheter 800 shows a horizontal cross-sectional shape of the balloon 806 with respect to the a horizontal cross-sectional shape of the catheter body. The balloon has a C shape with an opening 1204. In particular, the balloon is formed substantially around the circumference of the catheter body while leaving a portion of the catheter body exposed, forming a channel 808 between the balloon and the catheter body. The lower drainage hole (not show) is provided on the catheter body within the channel 808 and forms an opening into the inner lumen 820. The balloon drainage hole 1102 of the outer lumen 816 opens up to the balloon to allow for inflation or filling of the balloon. In an aspect, a torus 1202 is formed within the balloon to allow for even dispersion of gas or water from the balloon drainage hole 1102 to the balloon.

Figure 13:
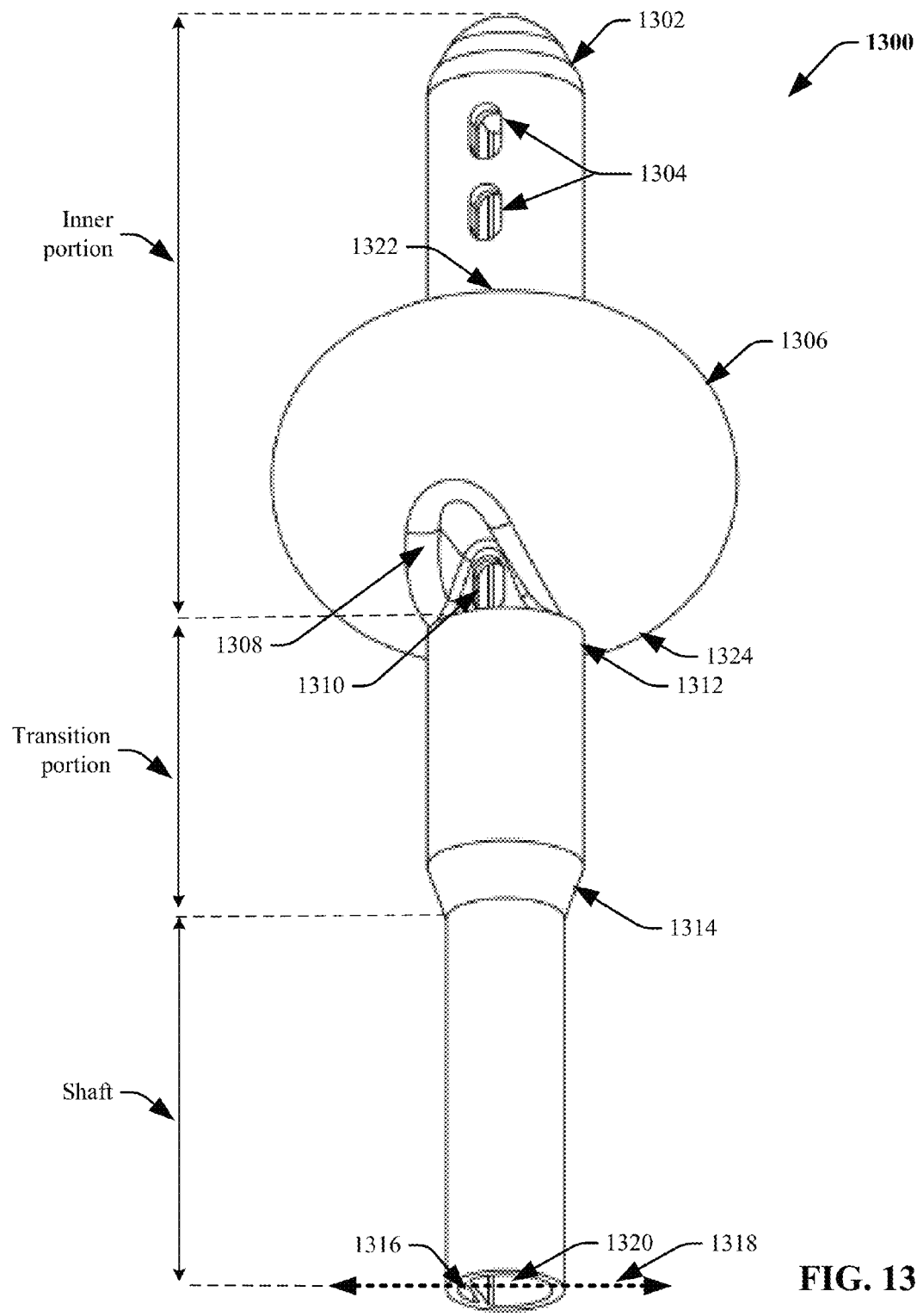
FIG. 13 presents a three dimensional view of another example tapered catheter having a balloon with a dome shaped crevice and a lower drainage hole provided within the crevice in accordance with various aspects and embodiments described herein.

FIG. 13 depicts a three dimensional view of the upper portion of another example tapered catheter 1300 in accordance with various aspects and embodiments disclosed herein. Catheter 1300 includes same or similar features and functionalities as catheter 800 with an alternative balloon design. Repetitive description of like elements employed in various catheters and/or techniques associated with usage of the various catheters is omitted for sake of brevity.

Similar to example catheter 800, catheter 1300 has a cylindrical body with varying diameters that decrease or tapper from a larger diameter at the proximal or inner end 1302 of the catheter to a smaller diameter at the outer or distal end (not shown) of the catheter. For example, catheter 1300 includes an inner portion, a transition zone and a shaft, wherein at least the OD of the shaft is smaller than that of the transition portion and the inner portion. Also similar to catheter 800, a lower part 1314 of the inner portion that connects to the shaft has varying diameters that form a funnel shape. It should be appreciated that although the lower portion of catheter 1300 (corresponding to the portion of the catheter that continues past dashed line 1318) is not depicted, this portion of the catheter can include various conventional catheter configurations and components, such as those depicted below dashed line 316 in FIG. 3. The dimensions and materials of the various components of catheter 800, including the inner portion, the transition portion, the shaft, the inner lumen 1320, the outer lumen 1316, etc., can correspond to those described for same or similar components of catheter 300. Repetitive description of like elements employed in various catheters and/or techniques associated with usage of the various catheters is omitted for sake of brevity.

Catheter 1300 exemplifies another unique design for the balloon 1306 of the inner portion of the catheter body that allows for inclusion of at least one lower drainage hole 1310 on the catheter body below and/or surrounded by at least a portion of the balloon 1306 (e.g., below the top surface 1322 of the balloon). This lower filling prevents and/or alleviates complications associated with an underactive bladder condition by allowing for complete emptying of urine in the bladder. In accordance with this embodiment, the lower drainage hole 1310 is located at or near the base 1312 of the inner portion of the catheter body below and/or surrounded by at least a portion of the balloon 1306. In order to include this lower drainage hole 1310, the balloon is formed with an irregular shape that includes at least one lip 1308 at the base of the balloon which forms a dome like opening or space between the base of the balloon and the body of the inner portion of the catheter. Accordingly, the lower drainage hole 1310 is provided at the base of the inner portion of the catheter body between the top surface 1322 and the bottom surface 1324 of the balloon 1306 within a dome structure 1308 of the balloon.

In an aspect, the balloon of catheter 1300 includes two or more lips 1308 or dome structures at the base thereof (e.g., on opposite sides of the balloon) with lower drainage holes respectively located on the catheter body inside the lips or dome structures. Catheter 1300 can also include one or more upper drainage holes 1304 and a similar inner and outer lumen configuration to that of catheter 800, wherein the outer lumen 1316 extends along a first side of the cylindrical body of the catheter and the inner lumen 820 extends along a second side of the cylindrical body.

Figure 14:
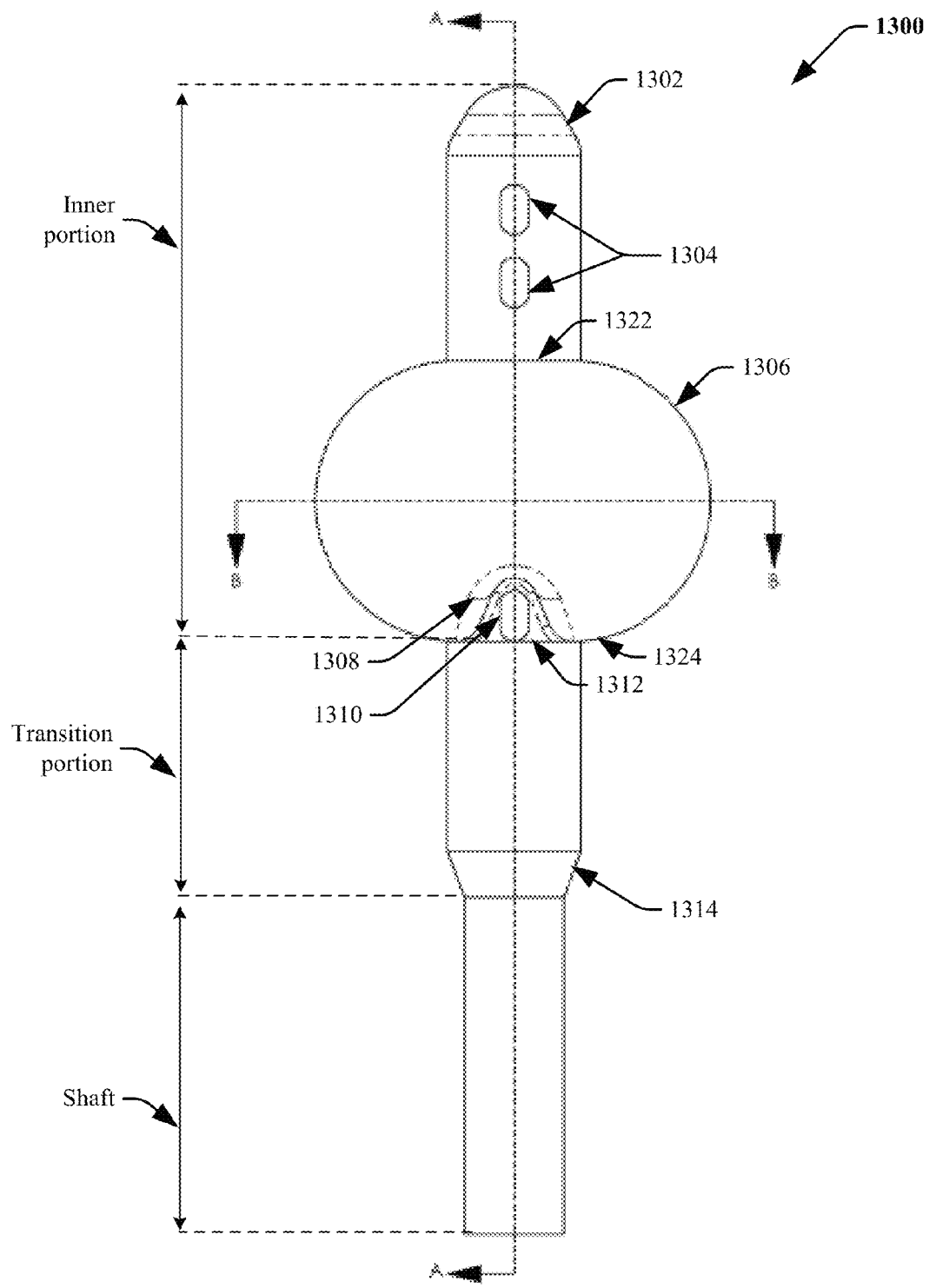
FIG. 14 presents a two dimensional view of the example tapered catheter having the balloon with the dome shaped crevice and the lower drainage hole provided within the channel in accordance with various aspects and embodiments described herein.

FIG. 14 depicts a two dimensional view of the upper portion of example tapered catheter 1300 in accordance with various aspects and embodiments disclosed herein. Repetitive description of like elements employed in various catheters and/or techniques associated with usage of the various catheters is omitted for sake of brevity.

Figure 15:
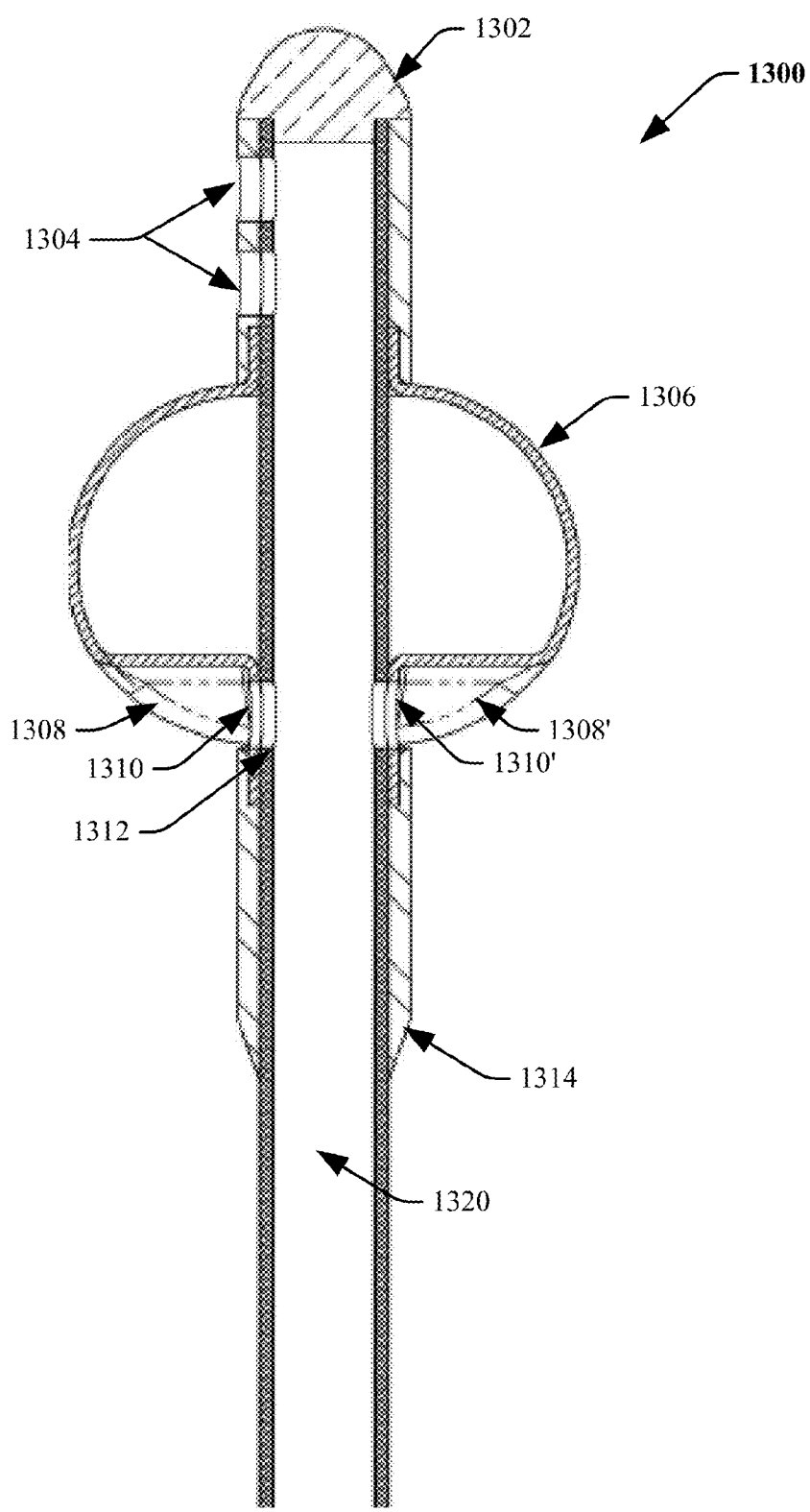
FIG. 15 presents a cross-sectional view of the example tapered catheter having the balloon with the dome shaped crevice and the lower drainage hole provided within the dome shaped crevice in accordance with various aspects and embodiments described herein.

FIG. 15 depicts a cross-sectional view of example tapered catheter 1300 taken along axis A-A identified in FIG. 14 in accordance with various aspects and embodiments disclosed herein. Repetitive description of like elements employed in various catheters and/or techniques associated with usage of the various catheters is omitted for sake of brevity.

This cross-sectional view of catheter 1300 depicts an embodiment wherein two lips 1308 and 1308' are included in the balloon 1306 and two lower drainage holes 1310 and 1310' respectively located on the catheter body within in the balloon lips. These lips 1308 and 1308' are provided on opposite sides of the balloon. The upper drainage holes 1304 and the lower drainage holes 1310 and 1310' open into the inner lumen 820.

Figure 16:
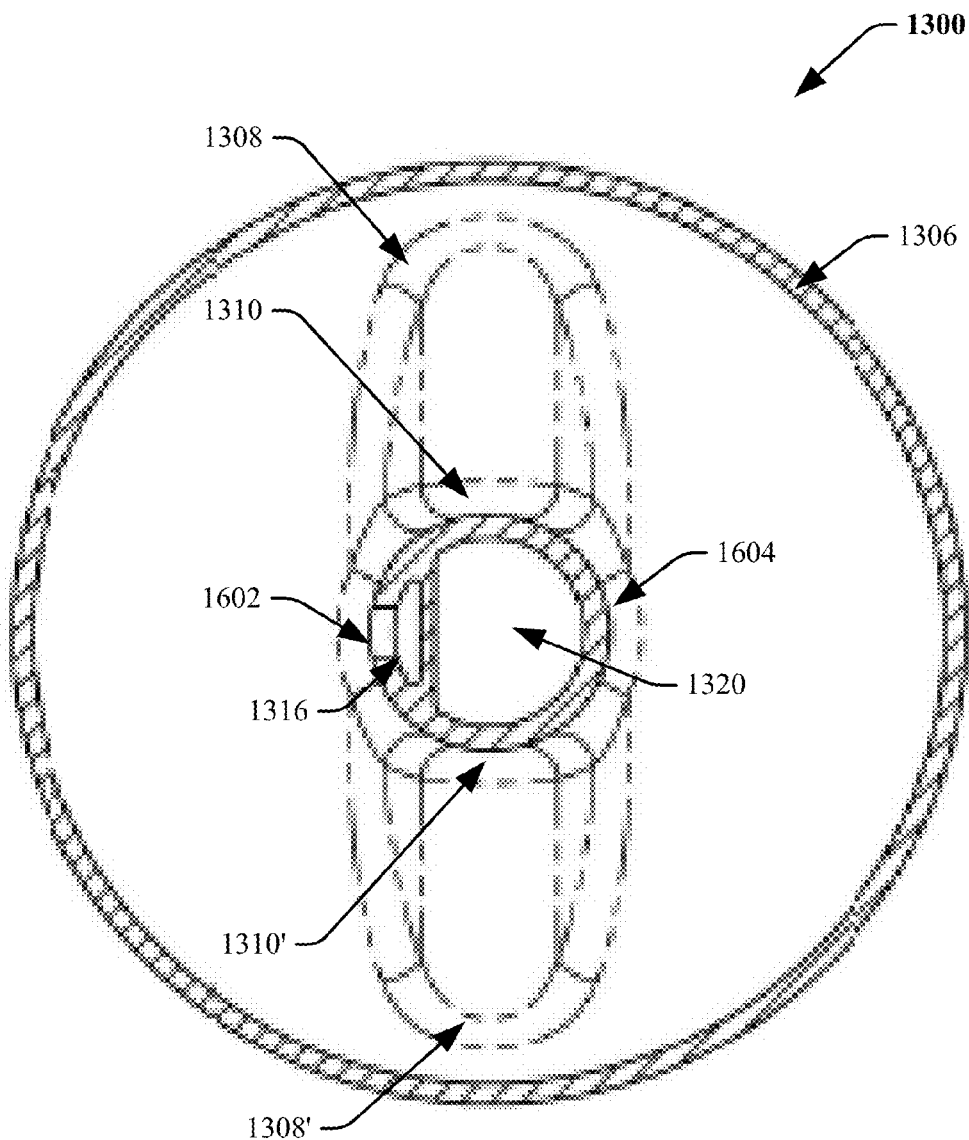
FIG. 16 presents another cross-sectional view of the example tapered catheter having the balloon with the dome shaped crevice and the lower drainage hole provided within the dome shaped crevice in accordance with various aspects and embodiments described herein.

FIG. 16 depicts a cross-sectional view of example tapered catheter 1300 taken along axis B-B identified in FIG. 14 in accordance with various aspects and embodiments disclosed herein. Repetitive description of like elements employed in various catheters and/or techniques associated with usage of the various catheters is omitted for sake of brevity.

This cross-sectional view of catheter 1300 also depicts two lips 1308 and 1308' included in the balloon 1306 and two lower drainage holes 1310 and 1310' respectively located on the catheter body within in the balloon lips. These lips 1308 and 1308' are provided on opposite sides of the balloon. Lower drainage holes 1310 and 1310' are located within the lips on the body of the catheter and open into the inner lumen 1320. The balloon is formed around the circumference of the catheter body while leaving portions of the catheter body within the lips 1308 and 1308' exposed. The outer lumen 1316 is located next to the inner lumen 1320 and includes a balloon drainage hole 1602 which opens up to the balloon 1306 to allow for inflation or filling of the balloon. In an aspect, a torus 1604 is formed within the balloon to allow for even dispersion of gas or water from the balloon drainage hole 1602 to the balloon 1306.

Figure 17:
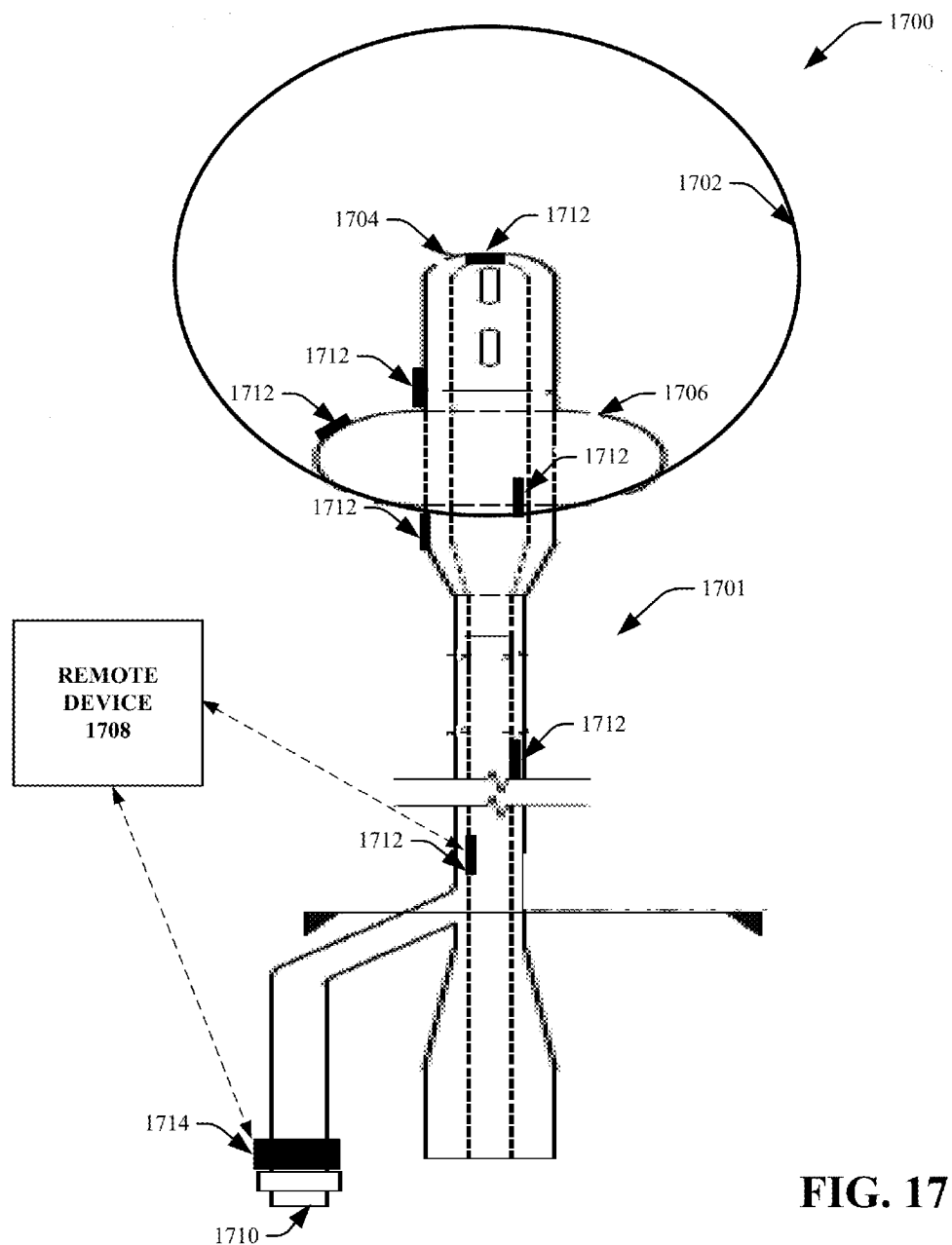
FIG. 17 illustrates an example catheter sensor system in accordance with various aspects and embodiments described herein.

FIG. 17 depicts an example catheter sensor system 1700 in accordance with various aspects and embodiments disclosed herein. Aspects of systems, apparatuses or processes explained in this disclosure can constitute machine-executable components embodied within machine(s), e.g., embodied in one or more computer readable mediums (or media) associated with one or more machines. Such components, when executed by the one or more machines, e.g., computer(s), computing device(s), virtual machine(s), etc. can cause the machine(s) to perform the operations described.

Catheter sensor system 1700 can include a tapered catheter 1701 and at least one remote device 1716 configured to communicate with the tapered catheter 1701. Tapered catheter 1701 can include one or more the various features and functionalities as other example tapered catheters described herein (e.g., catheters 300, 500, 800, 1300 and the like), with the addition of sensing capabilities afforded by one or more sensors 1712 integrated thereon. Repetitive description of like elements employed in various catheters and/or techniques associated with usage of the various catheters is omitted for sake of brevity.

Tapered catheter 1701 is depicted being worn inside the bladder 1702 of a patient. Tapered catheter 1701 is particularly configured with one or more sensors 1712 integrated on and/or within different components of the catheter body and/or balloon 1706. For example, a sensor 1712 can be located on an outside/external surface of the catheter body, on an internal surface of the catheter body, at or near the proximal end 1704 of the catheter, at or near the inner portion of the catheter, at or near the transition portion of the catheter, at or near the shaft of the catheter body, on or within the inner lumen, on or within the outer lumen, etc.

In an aspect, these sensors 1712 can send sensed information to a central processing circuit 1714 of the tapered catheter at which the sensed information is processed and/or communicated to a remote device 1708. In accordance with this aspect, the one or more sensors 1712 can be electrically coupled (e.g., via one or more wires and/or wirelessly) to the central processing circuit to facilitate sensing functions of the one or more sensors 1712, analyzing information sensed by the one or more sensors 1712, and wirelessly communicating information associated with information sensed by the one or more sensors to the remote device 1708. Central processing circuit 1714 is described in greater detail with reference to FIG. 18.

Although the central processing circuit 1714 is depicted being located at or near a valve 1710 associated with the outer (balloon filling) lumen and provided outside of the body when the catheter is worn by a patient, it should be appreciated that the central processing unit can be provided at other locations on the catheter body. For example, the central processing circuit 1714 can be located at or near the transition portion of the catheter body on an internal or external surface of the catheter body. In another aspect, the one or more sensors 1712 can be configured to communicate sensed information directly (e.g., wirelessly) to the remote device 1708 for processing thereof.

In an aspect, these one or more sensors 1712 can facilitate proper insertion and placement of the catheter 1701 into the urinary tract and/or gather information related to catheter movement while the catheter remains inside the patient. For example, the one or more sensors can include a camera, a pressure sensor, and/or a motion sensor (e.g., an accelerometer, a gyroscope, etc.). As the catheter 1701 is inserted into the urinary tract, one or more cameras can capture image data that can be rendered at the remote device 1708 (e.g., via a display). The image data can be used by the medical caregiver performing catheterization to properly place the catheter inside the bladder 1702 and inflate the balloon 1706. After the catheter is in place, image data can be periodically collected to capture urine levels and other visual characteristics associated with the bladder and the urinary tract (e.g., redness, swelling, development of blockages, infection, etc.). In another example, pressure and/or motion sensors can facilitate detection of movement (e.g., improper shifting) of the catheter after the catheter has been inserted into the patient.

In another aspect, the one or more sensors 1712 can sense information regarding bladder function and condition. For example, pressure and/or motion sensors can capture information regarding urine flow and muscle contraction. In another example, temperature and pressure sensors can be employed to monitor temperatures within the bladder and urinary tract as well as inflammation. Still in yet another aspect, the one or more sensors 1712 can include biosensors configured to detect various analytes present in the patient's urinary tract and/or urine and/or various characteristics of the patients urine to facilitate real-time and continuous urinalysis. For example, these biosensors can detect various ions and trace metals in the urine, including but not limited to: nitrite, sodium, potassium, urinary calcium, and phosphate. In another example, these biosensors can detect different proteins and hormones present in the urine (e.g., cystatin C, human chorionic gonadotropin, etc.) as well as the presence of blood cells (red and white) and hemoglobin. Other molecules that can be detected using biosensors can include but are not limited to: glucose, ketone bodies, bilirubin, urobilinogen, creatinine, free catecholamines dopamine, free cortisol, phenylalanin. In another example, sensors 1712 can include biosensors configured to detect concentration of drugs in the urine (e.g., methotrexate or salicylates) and urine characteristics, such as pH levels.

In an aspect, information captured/sensed by sensors 1712 is sent to remote device 1708 at which the information is processed to determine or infer various medical/health parameters associated therewith (e.g., to perform urinanalysis). In another aspect, central processing circuit 1714 can provide on board processing of information sensed by sensors 1712 and report processed information to the remote device. Remote device 1708 can include any suitable computing device associated with a user and configured to communicate with the one or more sensors 1712 and/or the central processing circuit 1714. For example, remote device 1708 can include a desktop computer, a laptop computer, a mobile phone, a smartphone, a tablet personal computer (PC), a personal digital assistant PDA, a wearable computing device, a television, or an Internet enabled television. As used in this disclosure, the terms "consumer" or "user" refers to a person, entity, system, or combination thereof that employs system 1700 (or additional systems described in this disclosure) using a remote device 1708. For example, remote device 1708 can include a personal device employed by the patient wearing or associated with catheter 1701. According to this example, the patient can receive information regarding analytes sensed by the catheter and/or determined or inferred (e.g., via processing software provided on the remote device 1708 and/or the central processing circuit) physical states/conditions of the patient. In another example, the remote device 1708 can include a device employed by a medical caregiver at location remote from the patient. In yet another example, remote device 1708 can include a computing system/server configured to gather information from patients wearing catheter 1701.

Remote device 1708 can communicate with sensors 1712 and/or central processing circuit 1714 using various wired and/or wireless networks, including but not limited to, a cellular network, a wide area network (WAD, e.g., the Internet), a local area network (LAN), or a personal area network (PAN). For example, remote device 1708 can communicate with sensors 1712 and/or central processing circuit 1714 (and vice versa) using virtually any desired wired or wireless technology, including, for example, cellular, WAN, wireless fidelity (Wi-Fi), Wi-Max, WLAN, near field communication (NFC), Bluetooh™, etc. In an aspect, one or more components of system 1700 are configured to interact via disparate networks.

Figure 18:
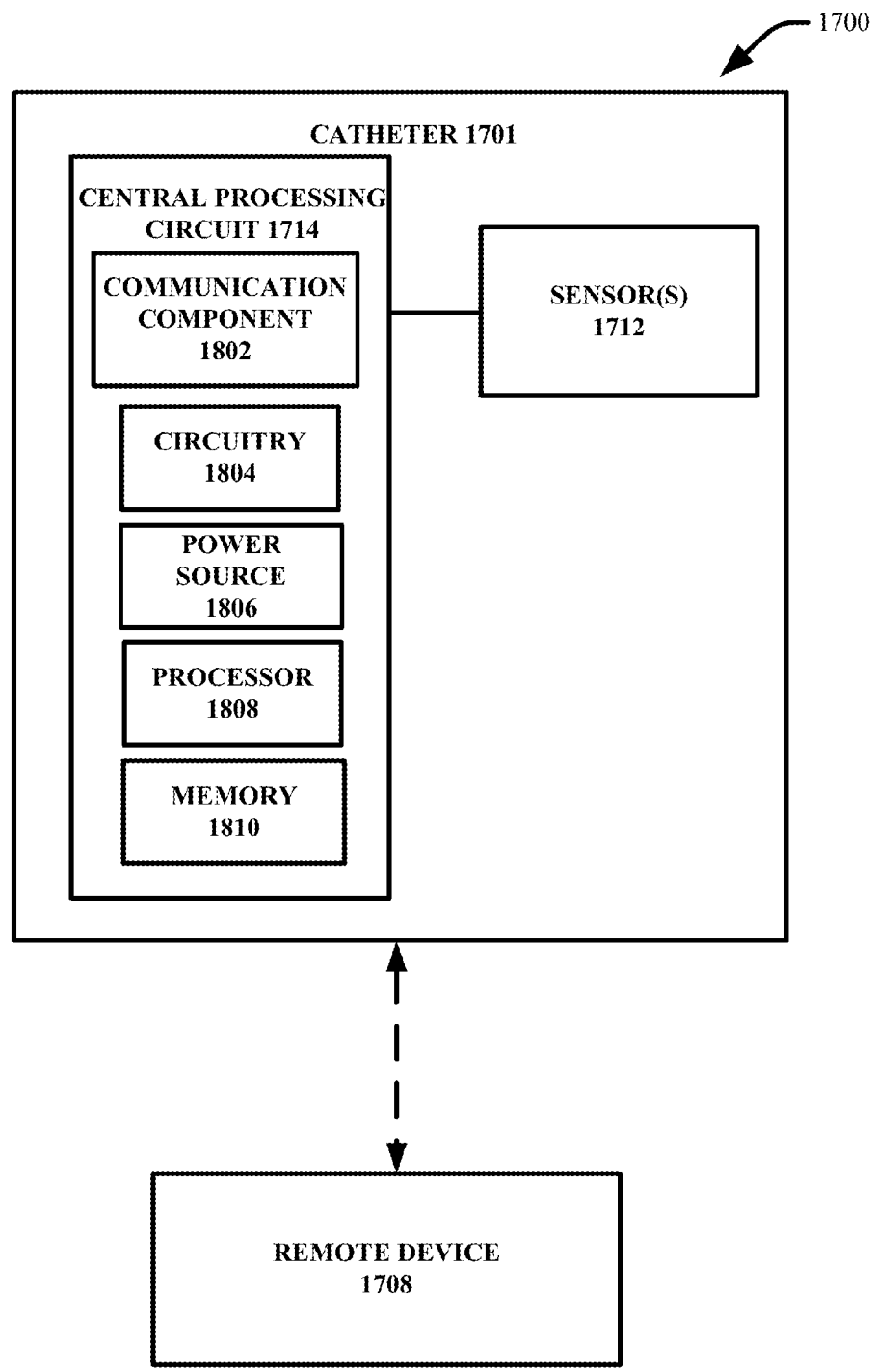
FIG. 18 illustrates a high level block diagram of the example catheter sensor system in accordance with various aspects and embodiments described herein.

FIG. 18 presents a high level block diagram of example catheter sensor system 1700 in accordance with various aspects and embodiments described herein. Repetitive description of like elements employed in various catheters and/or techniques associated with usage of the various catheters is omitted for sake of brevity.

Catheter 1701 can include central processing circuit 1714 and one or more sensors 1712 including but not limited to: imaging sensors (e.g., a camera), pressure sensors, motion sensors, thermal sensor, and/or biosensors. Central processing circuit 1714 can include communication component 1802, circuitry 1804, power source 1806, processor 1808, and memory 1810. In various embodiments, one or more of the sensors 1712, communication component 1802, circuitry 1804, power source 1806, processor 1808, and memory 1810 can be electrically or chemically coupled to one another to perform one or more functions of the central processing circuit 1714. For example, one or more wires can connect the components of central processing circuit 1714 and the one or more sensors 1712. Central processing circuit 1714 can include memory 1810 for storing computer executable components and instructions and processor 1808 can facilitate operation of the computer executable components and instructions by central processing circuit 1714.

Central processing circuit 1714 can include communication component 1802 to facilitate sending and receiving wireless communications regarding information sensed by one or more sensors, such as image data, motion data, pressure data, temperature data, analyte data, etc. For example, the communication component can include a receiver, a transmitter, a transceiver and/or a transducer. In an aspect, the communication component 1802 includes a radio frequency (RF) antenna. In an aspect, the communication component 1802 can transmit sensed and/or processed information in response to a request from remote device 1708.

In various aspects, sensed signals captured by the one or more sensors 1712 are wirelessly transmitted to remote device 1708 for subsequent processing thereof. However, in another aspect, central processing circuit 1714 performs on board processing of sensed signals. For example, processor 1808 can determine presence and/or concentration of a sensed analyte based on signals generated by the one or more sensors. Processor 1808 can further determine or infer various medical parameters, conditions, and/or states based on the sensed analyte concentration (e.g., presence of infection). In order to processes information generated by the one or more sensors, in an aspect, sensed signals can be stored in memory 1810. Further, memory 1810 can store various look-up tables and/or algorithms relating sensed information to analyte concentration and/or health parameters/conditions.

In an embodiment, processor 1808 can employ various (explicitly or implicitly trained) classification schemes or systems (e.g., support vector machines, neural networks, expert systems, Bayesian belief networks, fuzzy logic, data fusion engines, etc.) in connection with performing analysis of sensed signals at the one or more sensors 1712. A classifier can map an input attribute vector, x=(x1, x2, x3, x4 . . . , xn), to a confidence that the input belongs to a class, such as by f(x)=confidence(class). Such classification can employ a probabilistic or statistical-based analysis (e.g., factoring into the analysis utilities and costs) to prognose or infer a state of the urine. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used in this disclosure also is inclusive of statistical regression that is utilized to develop models of priority.

Central processing circuit 1714 can additionally include the appropriate circuitry 1804 to facilitate the functions of the central processing circuit For example, circuitry can facilitate the transfer of signals received at the one or more sensor 1714 to the communication component 1802, memory 1810, and/or processor 1808. Circuitry 1804 can also include signal processing hardware and software, (e.g. amplifiers, modulators, and etc.) for processing electrical signals received at the one or more sensors 1712 for wireless transmission thereof.

Central processing circuit 1714 can also include a power source 1806. Power source 1806 can include any suitable power source that can provide necessary power for the operation of various components of the central processing circuit 1714 and/or the one or more sensors 1712. For example, the power source 1806 can include but is not limited to a battery, a capacitor, a solar power source, or a mechanically derived power source (e.g., MEMs system). In an aspect, central processing circuit 1714 does not require an onboard power source to operate. For example, central processing circuit 1714 can receive power via wireless energy transfer (e.g. using electromagnetic inductance techniques and related components).

Figure 19:
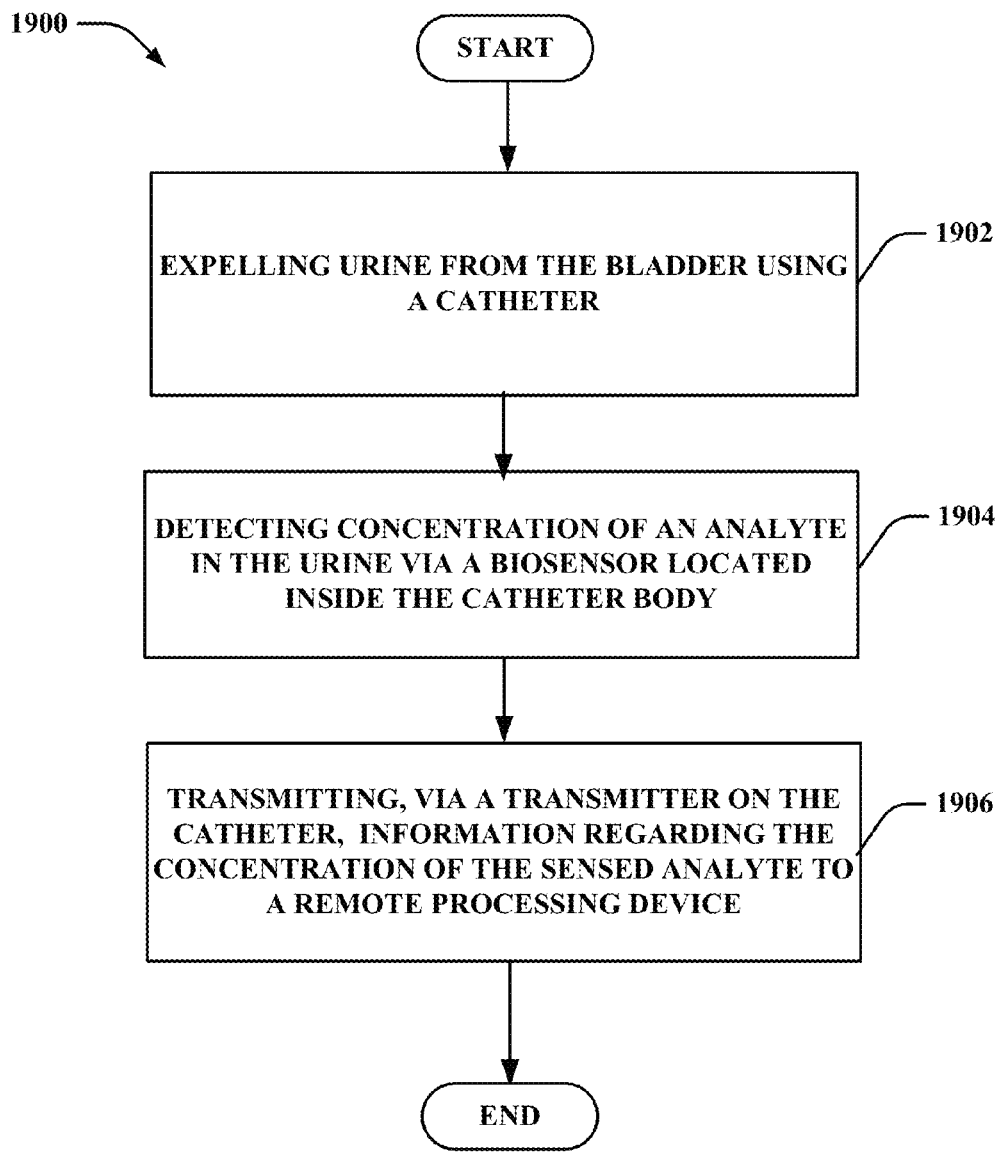
FIG. 19 provides a method for urinalysis using a catheter sensor system in accordance with various aspects and embodiments described herein.

FIG. 19 illustrates a method for performing real-time urinanalysis using a catheter in accordance with certain aspects of this disclosure. At 1902, urine is expelled from the bladder using a catheter (e.g., catheter 1701). At 1904, concentration of an analyte in the urine is detected via a biosensor located inside the catheter body. For example, the biosensor can be configured to detect presence and concentration of various molecules, ions, proteins, hormones, etc., in the urine that can be used to diagnose and monitor a wide variety of health states and conditions of the patient (e.g., urinary tract infections, kidney disease, diabetes, etc.). At 1906, information regarding the concentration of the analyte is transmitted to a remote processing device. For example, the catheter (e.g., via the a transmitter associated with the biosensor) can send raw data signals regarding the sensed analyte to the remote processing device for processing thereof. In another example, the catheter can include onboard processing capabilities to analyze and determine patient health parameters and states based on the concentration of the sensed analyte. According to this example, the catheter can transmit processed information to the remote device regarding diagnosis based on the sensed analyte.

While, for purposes of simplicity of explanation, the method is described as a series of acts, it is to be understood and appreciated that this disclosure is not limited by the order of acts, as some acts may occur in different orders and/or concurrently with other acts from that shown and described herein. For example, those skilled in the art will understand and appreciate that methods can alternatively be represented as a series of interrelated states or events, such as in a state diagram. Moreover, not all illustrated acts may be required to implement methods in accordance with certain aspects of this disclosure.

EXAMPLE OPERATING ENVIRONMENTS

The systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which may be explicitly illustrated in this disclosure.

Figure 20:
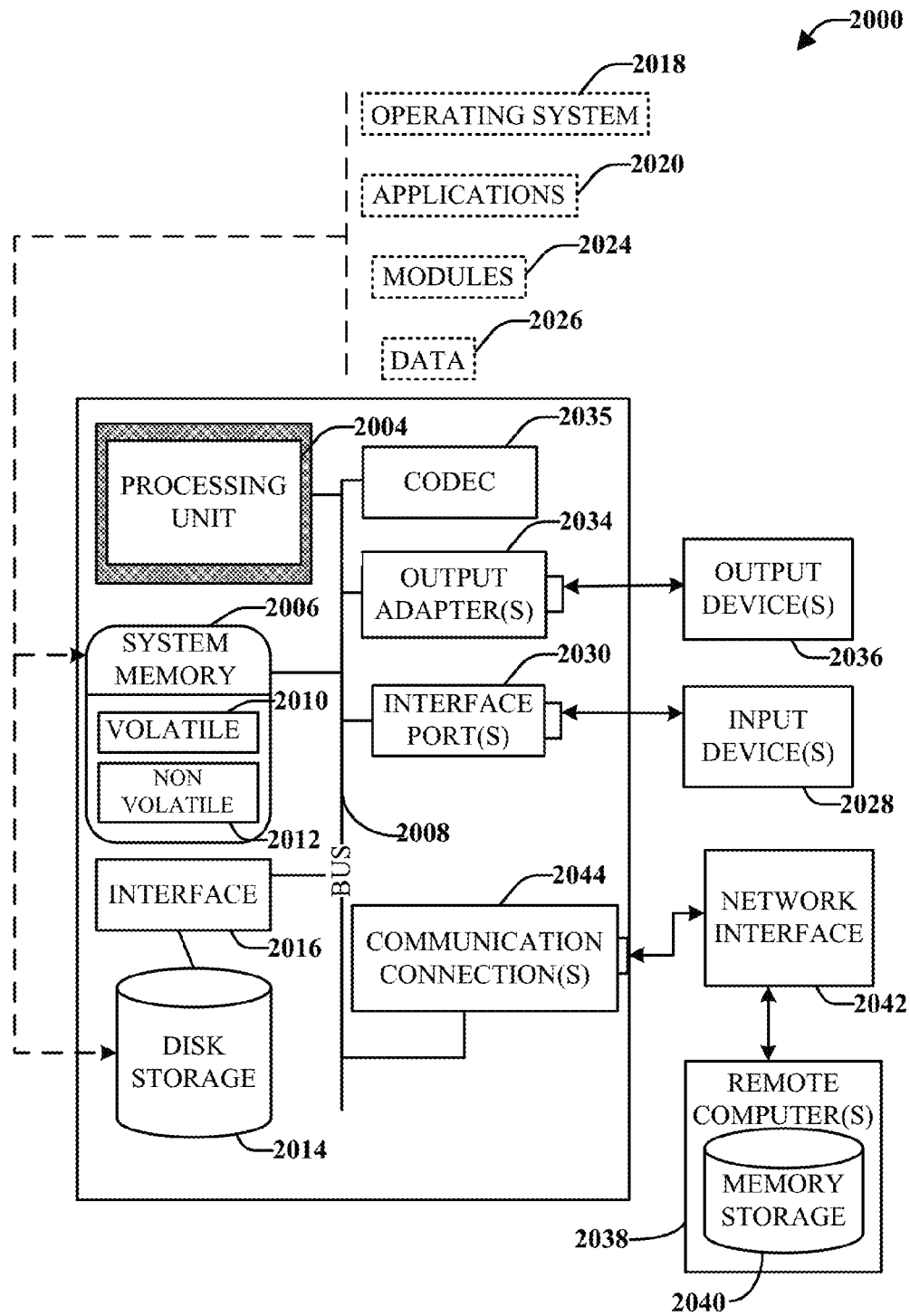
FIG. 20 is an illustration of a schematic diagram of an exemplary networked or distributed computing environment with which one or more aspects described herein can be associated.

With reference to FIG. 20, a suitable environment 2000 for implementing various aspects of the claimed subject matter includes a computer 2002. The computer 2002 includes a processing unit 2004, a system memory 2006, a codec 2005, and a system bus 2008. The system bus 2008 couples system components including, but not limited to, the system memory 2006 to the processing unit 2004. The processing unit 2004 can be any of various available processors. Dual microprocessors and other multiprocessor architectures also can be employed as the processing unit 2004.

The system bus 2008 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 13204), and Small Computer Systems Interface (SCSI).

The system memory 2006 includes volatile memory 2010 and non-volatile memory 2012. The basic input/output system (BIOS), containing the basic routines to transfer information between elements within the computer 2002, such as during start-up, is stored in non-volatile memory 2012. In addition, according to present innovations, codec 2005 may include at least one of an encoder or decoder, wherein the at least one of an encoder or decoder may consist of hardware, a combination of hardware and software, or software. Although, codec 2005 is depicted as a separate component, codec 2005 may be contained within non-volatile memory 2012. By way of illustration, and not limitation, non-volatile memory 2012 can include read only memory (ROM), programmable ROM (PROM), electrically programmable ROM (EPROM), electrically erasable programmable ROM (EEPROM), or flash memory. Volatile memory 2010 includes random access memory (RAM), which acts as external cache memory. According to present aspects, the volatile memory may store the write operation retry logic (not shown in FIG. 20) and the like. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM.

Computer 2002 may also include removable/non-removable, volatile/non-volatile computer storage medium. FIG. 20 illustrates, for example, disk storage 2014. Disk storage 2014 includes, but is not limited to, devices like a magnetic disk drive, solid state disk (SSD) floppy disk drive, tape drive, Jaz drive, Zip drive, LS-70 drive, flash memory card, or memory stick. In addition, disk storage 2014 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 2014 to the system bus 2008, a removable or non-removable interface is typically used, such as interface 2016.

It is to be appreciated that FIG. 20 describes software that acts as an intermediary between users and the basic computer resources described in the suitable operating environment 2000. Such software includes an operating system 2018. Operating system 2018, which can be stored on disk storage 2014, acts to control and allocate resources of the computer system 2002. Applications 2020 take advantage of the management of resources by operating system 2018 through program modules 2024, and program data 2026, such as the boot/shutdown transaction table and the like, stored either in system memory 2006 or on disk storage 2014. It is to be appreciated that the claimed subject matter can be implemented with various operating systems or combinations of operating systems.

A user enters commands or information into the computer 2002 through input device(s) 2028. Input devices 2028 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 2004 through the system bus 2008 via interface port(s) 2030. Interface port(s) 2030 include, for example, a serial port, a parallel port, a game port, and a universal serial bus (USB). Output device(s) 2036 use some of the same type of ports as input device(s). Thus, for example, a USB port may be used to provide input to computer 2002, and to output information from computer 2002 to an output device 2036. Output adapter 2034 is provided to illustrate that there are some output devices 2036 like monitors, speakers, and printers, among other output devices 2036, which require special adapters. The output adapters 2034 include, by way of illustration and not limitation, video and sound cards that provide a means of connection between the output device 2036 and the system bus 2008. It should be noted that other devices and/or systems of devices provide both input and output capabilities such as remote computer(s) 2038.

Computer 2002 can operate in a networked environment using logical connections to one or more remote computers, such as remote computer(s) 2038. The remote computer(s) 2038 can be a personal computer, a server, a router, a network PC, a workstation, a microprocessor based appliance, a peer device, a smart phone, a tablet, or other network node, and typically includes many of the elements described relative to computer 2002. For purposes of brevity, only a memory storage device 2040 is illustrated with remote computer(s) 2038. Remote computer(s) 2038 is logically connected to computer 2002 through a network interface 2042 and then connected via communication connection(s) 2044. Network interface 2042 encompasses wire and/or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 2044 refers to the hardware/software employed to connect the network interface 2042 to the bus 2008. While communication connection 2044 is shown for illustrative clarity inside computer 2002, it can also be external to computer 2002. The hardware/software necessary for connection to the network interface 2042 includes, for exemplary purposes only, internal and external technologies such as, modems including regular telephone grade modems, cable modems and DSL modems, ISDN adapters, and wired and wireless Ethernet cards, hubs, and routers.

Figure 21:
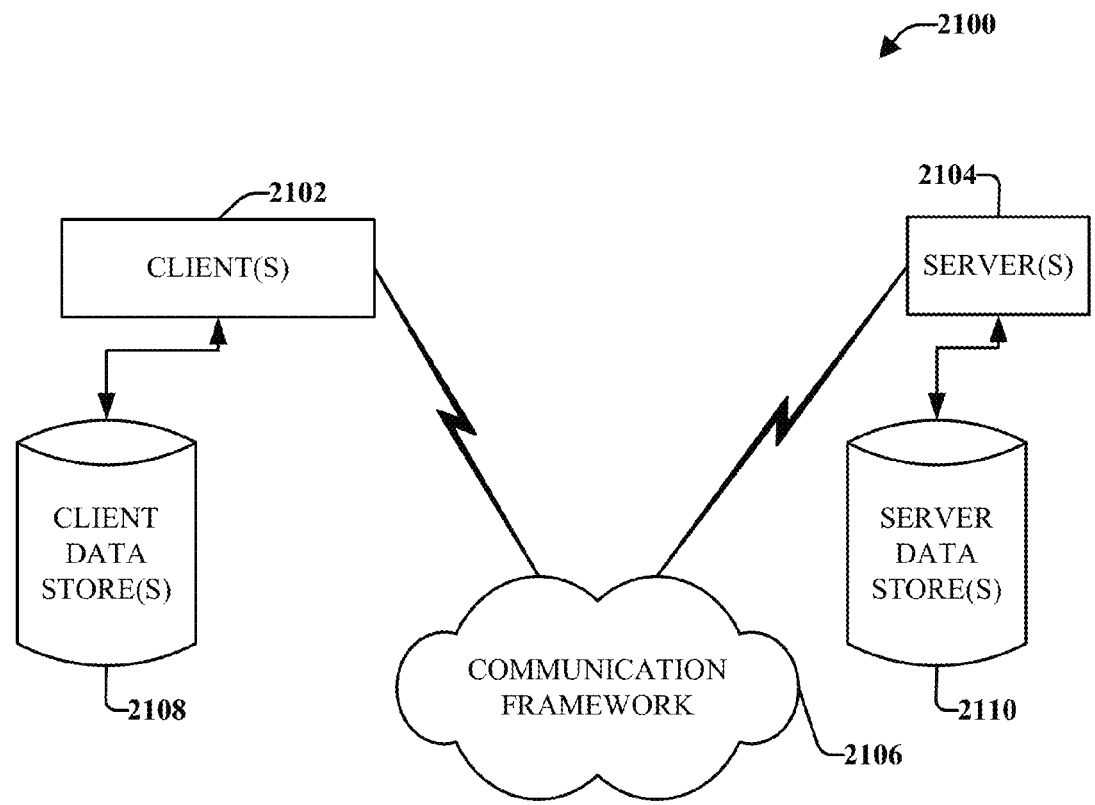
FIG. 21 is an illustration of a schematic diagram of an exemplary computing environment with which one or more aspects described herein can be associated.

Referring now to FIG. 21, there is illustrated a schematic block diagram of a computing environment 2100 in accordance with this disclosure. The system 2100 includes one or more client(s) 2102 (e.g., laptops, smart phones, PDAs, media players, computers, portable electronic devices, tablets, and the like). The client(s) 2102 can be hardware and/or software (e.g., threads, processes, computing devices). The system 2100 also includes one or more server(s) 2104. The server(s) 2104 can also be hardware or hardware in combination with software (e.g., threads, processes, computing devices). The servers 2104 can house threads to perform transformations by employing aspects of this disclosure, for example. One possible communication between a client 2102 and a server 2104 can be in the form of a data packet transmitted between two or more computer processes wherein the data packet may include video data. The data packet can include a metadata, e.g., associated contextual information, for example. The system 2100 includes a communication framework 2106 (e.g., a global communication network such as the Internet, or mobile network(s)) that can be employed to facilitate communications between the client(s) 2102 and the server(s) 2104.

Communications can be facilitated via a wired (including optical fiber) and/or wireless technology. The client(s) 2102 include or are operatively connected to one or more client data store(s) 2108 that can be employed to store information local to the client(s) 2102 (e.g., associated contextual information). Similarly, the server(s) 2104 are operatively include or are operatively connected to one or more server data store(s) 2110 that can be employed to store information local to the servers 2104.

In one embodiment, a client 2102 can transfer an encoded file, in accordance with the disclosed subject matter, to server 2104. Server 2104 can store the file, decode the file, or transmit the file to another client 2102. It is to be appreciated, that a client 2102 can also transfer uncompressed file to a server 2104 and server 2104 can compress the file in accordance with the disclosed subject matter. Likewise, server 2104 can encode video information and transmit the information via communication framework 2106 to one or more clients 2102.

The illustrated aspects of the disclosure may also be practiced in distributed computing environments where certain tasks are performed by remote processing devices that are linked through a communications network. In a distributed computing environment, program modules can be located in both local and remote memory storage devices.

Moreover, it is to be appreciated that various components described in this description can include electrical circuit(s) that can include components and circuitry elements of suitable value in order to implement the embodiments of the subject innovation(s). Furthermore, it can be appreciated that many of the various components can be implemented on one or more integrated circuit (IC) chips. For example, in one embodiment, a set of components can be implemented in a single IC chip. In other embodiments, one or more of respective components are fabricated or implemented on separate IC chips.

What has been described above includes examples of the embodiments of the present invention. It is, of course, not possible to describe every conceivable combination of components or methodologies for purposes of describing the claimed subject matter, but it is to be appreciated that many further combinations and permutations of the subject innovation are possible. Accordingly, the claimed subject matter is intended to embrace all such alterations, modifications, and variations that fall within the spirit and scope of the appended claims. Moreover, the above description of illustrated embodiments of the subject disclosure, including what is described in the Abstract, is not intended to be exhaustive or to limit the disclosed embodiments to the precise forms disclosed. While specific embodiments and examples are described in this disclosure for illustrative purposes, various modifications are possible that are considered within the scope of such embodiments and examples, as those skilled in the relevant art can recognize.

In particular and in regard to the various functions performed by the above described components, devices, circuits, systems and the like, the terms used to describe such components are intended to correspond, unless otherwise indicated, to any component which performs the specified function of the described component (e.g., a functional equivalent), even though not structurally equivalent to the disclosed structure, which performs the function in the disclosure illustrated exemplary aspects of the claimed subject matter. In this regard, it will also be recognized that the innovation includes a system as well as a computer-readable storage medium having computer-executable instructions for performing the acts and/or events of the various methods of the claimed subject matter.

The aforementioned systems/circuits/modules have been described with respect to interaction between several components/blocks. It can be appreciated that such systems/circuits and components/blocks can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described in this disclosure may also interact with one or more other components not specifically described in this disclosure but known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

As used in this application, the terms "component," "module," "system," or the like are generally intended to refer to a computer-related entity, either hardware (e.g., a circuit), a combination of hardware and software, software, or an entity related to an operational machine with one or more specific functionalities. For example, a component may be, but is not limited to being, a process running on a processor (e.g., digital signal processor), a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. Further, a "device" can come in the form of specially designed hardware; generalized hardware made specialized by the execution of software thereon that enables the hardware to perform specific function; software stored on a computer readable storage medium; software transmitted on a computer readable transmission medium; or a combination thereof.

Moreover, the words "example" or "exemplary" are used in this disclosure to mean serving as an example, instance, or illustration. Any aspect or design described in this disclosure as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Computing devices typically include a variety of media, which can include computer-readable storage media and/or communications media, in which these two terms are used in this description differently from one another as follows. Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal that can be transitory such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

APPENDIX A

Proposed Foley Catheter Sizing

| | ID (mm) Proximal | | ID (mm) Distal | | OD (mm) distal with existing wall thickness | | | OD (Fr) | OD (mm) distal with proposed wall thickness | | | OD (Fr) | Wall Thickness | |
|---|---|---|---|---|---|---|---|---|---|---|---|---|---|---|
| Ch/Fr | Existing | Proposed | Existing | Proposed | Existing | Proposed | % Reduction | Proposed | Existing | Proposed | % Reduction | Proposed | Existing | Proposed |
| 6 | 1.10 | 1.10 | 1.10 | 1.10 | 2.00 | 2.00 | 0.00% | 6 | 2.00 | 2.00 | 0.00% | 6 | 0.45 | 0.45 |
| 8 | 1.70 | 1.70 | 1.70 | 1.70 | 2.67 | 2.67 | 0.00% | 8 | 2.67 | 2.60 | -2.50% | 7.8 | 0.483333 | 0.45 |
| 10 | 2.30 | 2.30 | 2.30 | 2.00 | 3.33 | 3.03 | -9.00% | 9.1 | 3.33 | 2.90 | -13.00% | 8.7 | 0.516667 | 0.45 |
| 12 | 2.80 | 2.80 | 2.80 | 2.00 | 4.00 | 3.20 | -20.00% | 9.6 | 4.00 | 2.90 | -27.50% | 8.7 | 0.6 | 0.45 |
| 14 | 3.30 | 3.30 | 3.30 | 2.00 | 4.67 | 3.37 | -27.86% | 10.1 | 4.67 | 2.90 | -37.86% | 8.7 | 0.683333 | 0.45 |
| 16 | 3.80 | 3.80 | 3.80 | 2.00 | 5.33 | 3.53 | -33.75% | 10.6 | 5.33 | 2.90 | -45.63% | 8.7 | 0.766667 | 0.45 |
| 18 | 4.50 | 4.50 | 4.50 | 3.00 | 6.00 | 4.50 | -25.00% | 13.5 | 6.00 | 3.90 | -35.00% | 11.7 | 0.75 | 0.45 |
| 20 | 5.10 | 5.10 | 5.10 | 3.00 | 6.67 | 4.57 | -31.50% | 13.7 | 6.67 | 3.90 | -41.50% | 11.7 | 0.783333 | 0.45 |
| 22 | 5.60 | 5.60 | 5.60 | 3.00 | 7.33 | 4.73 | -35.45% | 14.2 | 7.33 | 3.90 | -46.82% | 11.7 | 0.866667 | 0.45 |
| 24 | 6.20 | 6.20 | 6.20 | 4.00 | 8.00 | 5.80 | -27.50% | 17.4 | 8.00 | 4.90 | -38.75% | 14.7 | 0.9 | 0.45 |
| 26 | 6.90 | 6.90 | 6.90 | 4.00 | 8.67 | 5.77 | -33.46% | 17.3 | 8.67 | 4.90 | -43.46% | 14.7 | 0.883333 | 0.45 |
| 28 | 7.60 | 7.60 | 7.60 | 4.00 | 9.33 | 5.73 | -38.57% | 17.2 | 9.33 | 4.90 | -47.50% | 14.7 | 0.866667 | 0.45 |
| 30 | 8.30 | 8.30 | 8.30 | 4.00 | 10.00 | 5.70 | -43.00% | 17.1 | 10.00 | 4.90 | -51.00% | 14.7 | 0.85 | 0.45 |

What is claimed is:

1. A urinary catheter, comprising:
a tubular body configured to insert into a urinary tract, the tubular body comprising:
an inner region configured to lie inside a bladder of the urinary tract when the tubular body is inserted into the urinary tract,
a shaft region configured to extend through a urethra of the urinary tract and outside the urinary tract when the tubular body is inserted into the urinary tract, wherein the inner region comprises a first diameter that is larger than a second diameter of the shaft region, and
a transition region located between the inner region and the shaft region of the tubular body and configured to lie outside and adjacent to an outer wall of the bladder when the tubular body is inserted into the urinary tract, wherein the transition region comprises a tapering diameter that tapers from the first diameter to the second diameter; and
an inner tube located within the tubular body, the inner tube comprising an inner portion corresponding to the inner region of the tubular body, a shaft portion corresponding to the shaft region of the tubular body, and a transition portion corresponding to the transition region of the tubular body, wherein the inner portion of the inner tube comprises a third diameter that is larger than a fourth diameter of the shaft portion of the inner tube, and wherein the transition portion comprises a tapering diameter that tapers from the third diameter to the fourth diameter.

2. The urinary catheter of claim 1, wherein the fourth diameter is less than or equal to about 51% to about 90% of the third diameter.

3. The urinary catheter of claim 1, wherein the transition region and the transition portion comprise a funnel shape.

4. The urinary catheter of claim 1, wherein the first diameter is about 28.0 Fr, the tapering diameter of the transition region tapers from about 28.0 Fr to about 10.0 Fr with a median diameter of 14.0 Fr, and the second diameter is about 10.0 Fr.

5. The urinary catheter of claim 1, wherein the inner region of the tubular body comprises a length of about 15.0 cm, the transition region comprises a length of about 1.5 cm, and the shaft region of the tubular body comprises a length of about 30.0 cm.

6. The urinary catheter of claim 1, further comprising:
an outer lumen comprising a cavity formed between the tubular body and the inner tube; and
an inner lumen comprising another cavity formed within the inner tube; and
two or more openings on the inner region of the tubular body that extend through the outer lumen and the inner tube and open into the inner lumen.

7. The urinary catheter of claim 6, further comprising:
a balloon attached to a lower part of the inner region of the tubular body and configured to rest inside the bladder when inflated or filled, wherein at least one of the two or more openings is located between the balloon and a urethral opening to the bladder.

8. The urinary catheter of claim 7, wherein when inflated or filled, the balloon comprises a disconnected ring shape that forms a channel between opposite ends of the ring shape.

9. The urinary catheter of claim 6, wherein the outer lumen comprises at least four channels that connect to the balloon for filling the balloon with gas or water, and wherein the at least four channels are provided at substantially evenly spaced positions from one another within the cavity of the outer lumen.

10. The urinary catheter of claim 6, wherein the inner lumen is coated with a material that has low friction to enhance urine flow.

11. The urinary catheter of claim 6, wherein the two or more openings are located between the balloon and a proximal end of the inner portion of the tubular body via which urine or other bodily secretions are collected when the catheter is located within the bladder.

12. The urinary catheter of claim 6, further comprising:
a balloon attached to a lower part of the inner region of the tubular body and configured to rest inside the bladder when inflated or filled, wherein when inflated or filled the balloon comprises a substantially spherical shape formed around the lower part of the inner region of the tubular body with a dome shaped hollow space formed at a base of the balloon, wherein at least one of the two or more openings is located at an area of the tubular body exposed within the dome shaped hollow space of the balloon.

13. The urinary catheter of claim 6, further comprising:
a balloon attached to a lower part of the inner region of the tubular body and configured to rest inside the bladder when inflated or filled, wherein when inflated or filled the balloon comprises a substantially spherical shape formed around the lower part of the inner region of the tubular body with two dome shaped indentions formed at a base of the balloon, wherein the two or more openings are respectively located at areas of the tubular body exposed via the dome shaped indentions.

14. The urinary catheter of claim 1, wherein an outer surface of the tubular body is coated with a material designed to reduce friction when the catheter is inserted into the urinary tract.

15. The urinary catheter of claim 1, wherein the tubular body is coated on inner and outer surfaces thereof with a biomimetic material to reduce or prevent bacterial or other microbial growth.

16. The urinary catheter of claim 1, wherein an outer surface of the tubular body is coated with a material that enhances mucosal growth.

17. The urinary catheter of claim 1, further comprising a removable introducer provided inside the tubular body configured to provide added rigidity to the tubular body when inserted into the urinary tract.

18. The urinary catheter of claim 17, wherein the removable introducer is enclosed within a sanitary bag that is sealed to a distal end of the shaft region of the tubular body, and wherein the introducer is sterilized within the sanitary bag.

19. A catheter comprising:
a tubular body configured to insert into a urinary tract, the tubular body comprising:
an inner region configured to lie inside a bladder of the urinary tract when the tubular body is inserted into the urinary tract,
a shaft region configured to extend through a urethra of the urinary tract and outside the urinary tract when the tubular body is inserted into the urinary tract, wherein the inner region comprises a first diameter that is larger than a second diameter of the shaft region, and
a transition region located between the inner region and the shaft region of the tubular body and configured to lie outside and adjacent to an outer wall of the bladder when the tubular body is inserted into the urinary tract, wherein the transition region comprises a tapering diameter that tapers from the first diameter to the second diameter;
an inner tube located within the tubular body, the inner tube comprising an inner portion corresponding to the inner region of the tubular body and a shaft portion corresponding to the shaft region of the tubular body, wherein the inner portion of the inner tube comprises a third diameter that is larger than a fourth diameter of the shaft portion of the inner tube, and wherein the transition portion comprises a tapering diameter that tapers from the third diameter to the fourth diameter;
an outer lumen comprising a cavity formed between the tubular body and the inner tube;
an inner lumen comprising another cavity formed within the inner tube;
a balloon attached to a lower part of the inner region of the tubular body and configured to rest inside the bladder when inflated or filled;
one or more upper drainage holes on the inner region of the tubular body that extend through the outer lumen and the inner tube and open into the inner lumen, wherein the one or more upper drainage holes are located between an upper surface of the balloon and a proximal end of the tubular body; and
one or more lower drainage holes on the inner region of the tubular body that extend through the inner tube and open into the inner lumen, wherein the one or more lower drainage holes are located between an upper surface of the balloon and a lower surface of the balloon.

20. The catheter of claim 19, wherein the balloon has a shape that exposes a lower surface of the inner region of the tubular body between the upper and lower surfaces of the balloon when inflated, and wherein the one or more lower drainage holes are located on the lower surface of inner region of the tubular body.

21. The catheter of claim 19, wherein the balloon has a shape that forms a channel between the balloon and an external surface of the tubular body when inflated, and wherein the one or more lower drainage holes are located within the channel.

22. The catheter of claim 19, wherein the transition region and the transition portion comprise a funnel shape.

23. The catheter of claim 19, wherein the balloon has a shape that forms a dome over a portion of an external surface of the tubular body when inflated or filled, and wherein at least one of the lower drainage holes is located within the dome.

24. A urinary catheter, comprising:
an outer lumen formed via an external tubular body configured to insert into a urinary tract of a patient; and
an inner lumen formed via an internal tubular body located within the external tubular body, wherein the outer lumen and the inner lumen respectively comprise:
an inner region configured to lie inside a bladder of the urinary tract when the external tubular body is inserted into the urinary tract,
a shaft region configured to extend through a urethra of the urinary tract and outside the urinary tract when the tubular body is inserted into the urinary tract, and
a transition region located between the inner region and the shaft region and configured to lie outside and adjacent to a base wall of the bladder when the external tubular body is inserted into the urinary tract,
wherein the outer lumen and the inner lumen respectively comprise first diameters at the inner region that are larger than second diameters at the shaft region, and tapering diameters at the transition region that taper from the first diameters to the second diameters.

25. The urinary catheter of claim 24, further comprising:
a balloon attached to the tubular body at a lower part of the inner region of the tubular body and configured to rest inside the bladder when inflated or filled; and
two or more lower drainage holes at the inner region of the tubular body that extend through the outer lumen and open to the inner lumen the inner tube, wherein the two or more lower drainage holes are located between an upper surface of the balloon and a lower surface of the balloon.

26. The urinary catheter of claim 25, further comprising:
wherein when inflated or filled, the balloon comprises a substantially spherical shape formed around the lower part of the inner region of the tubular body with a dome shaped hollow space formed at a base of the balloon, wherein at least one of the two or more openings is located at an area of the tubular body exposed within the dome shaped hollow space of the balloon.

27. The urinary catheter of claim 24, wherein the second diameters are less than or equal to about 80% of the first diameters.

28. The urinary catheter of claim 24, wherein the second diameters are less than or equal to about 51% of the first diameters.

29. The urinary catheter of claim 24, wherein the transition diameters are less than or equal to about 80% of the first diameters.

30. The urinary catheter of claim 24, wherein the transition diameters are less than or equal to about 60% of the first diameters.

* * * * *